Figure 4:
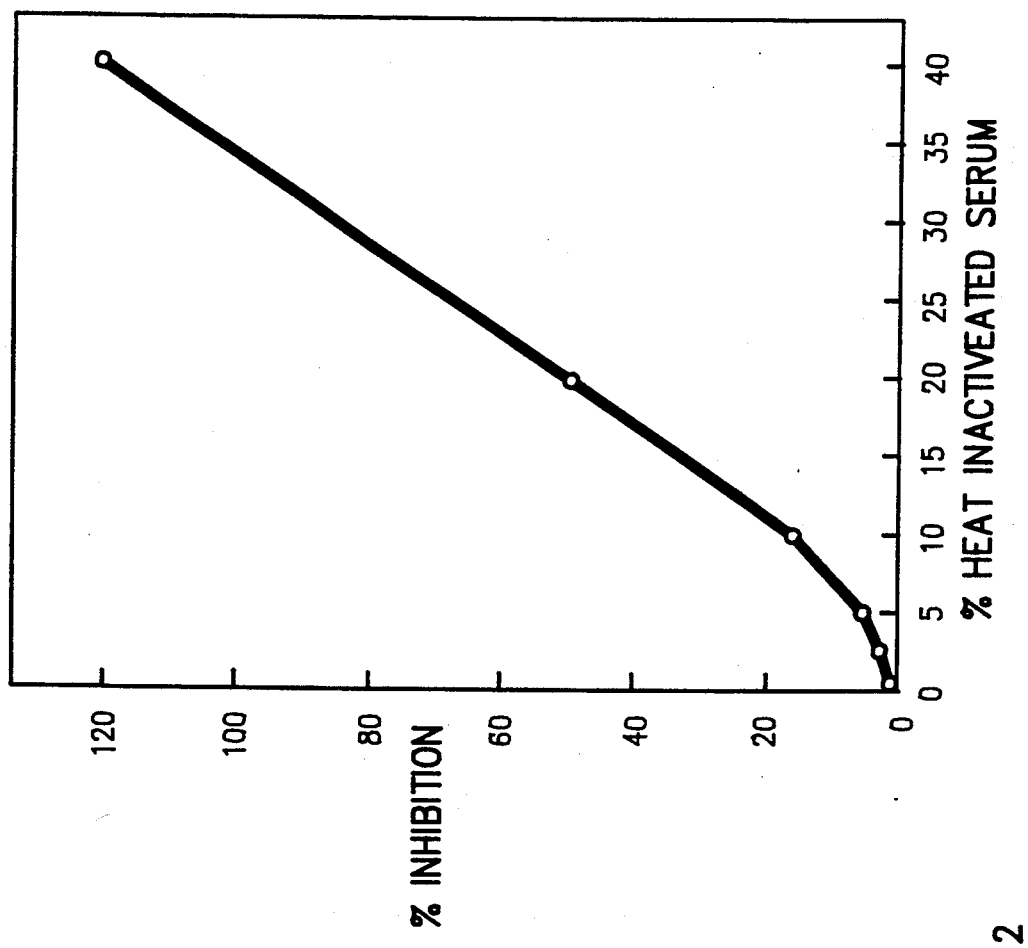

United States Patent [19]

Darveau et al.

[11] Patent Number: 5,409,898
[45] Date of Patent: Apr. 25, 1995

[54] COMPOSITIONS AND METHODS FOR TREATING INFECTIONS CAUSED BY ORGANISMS SENSITIVE TO BETA-LACTAM ANTIBIOTICS

[75] Inventors: Richard C. Darveau, Kirkland; James J. Blake, Seattle; Wesley J. Cosand, Bothell, all of Wash.

[73] Assignee: Bristol-Myers Squibb Company, New York, N.Y.

[21] Appl. No.: 233,203

[22] Filed: Apr. 26, 1994

Related U.S. Application Data

[63] Continuation of Ser. No. 655,321, Feb. 19, 1991, abandoned, which is a continuation-in-part of Ser. No. 484,020, Feb. 23, 1990, abandoned.

[51] Int. Cl.$^6$ ............... A61K 37/00; A61K 37/02; C07K 5/00; C07K 7/00
[52] U.S. Cl. ................... 514/13; 514/14; 514/12; 514/21; 530/324; 530/325; 530/326; 530/327
[58] Field of Search ............ 514/12, 13, 14, 21; 530/324, 325, 326, 327

[56] References Cited

U.S. PATENT DOCUMENTS

| | | | |
|---|---|---|---|
| 4,107,298 | 8/1978 | Lüning | 424/177 |
| 4,543,252 | 9/1985 | Lehrer et al. | 514/12 |
| 4,659,692 | 4/1987 | Lehrer et al. | 514/12 |
| 4,810,777 | 3/1989 | Zasloff | 530/326 |
| 5,045,531 | 9/1991 | Berkowitz | 514/12 |

FOREIGN PATENT DOCUMENTS

WO9012587 11/1990 WIPO ............ A61K 37/02

OTHER PUBLICATIONS

Zasloff, *P.N.A.S.*, vol. 84, 1987, pp. 5449–5453.
Zasloff et al., *P.N.A.S.*, vol. 85, 1988 pp. 910–913.
Christensen et al., *P.N.A.S.*, vol. 85, 1988, pp. 5072–5076.

*Primary Examiner*—Lester L. Lee
*Assistant Examiner*—A. M. Davenport
*Attorney, Agent, or Firm*—Brian W. Poor

[57] ABSTRACT

The invention is directed to compositions and methods for treating an infection caused by an organism susceptible to a β-lactam antibiotic comprising two or more active agents. In one embodiment, the composition comprises: (1) a β-lactam antibiotic and (2) a cationic oligopeptide. In another embodiment, the invention is also directed to a composition comprising: (1) a β-lactam antibiotic which inhibits the growth of Enterobacteriaceae bacteria and (2) at least one membrane active substance. Further, the invention is also directed to improved methods for screening potential bactericidal compositions in vitro wherein components of an active complement cascade are included.

44 Claims, 4 Drawing Sheets

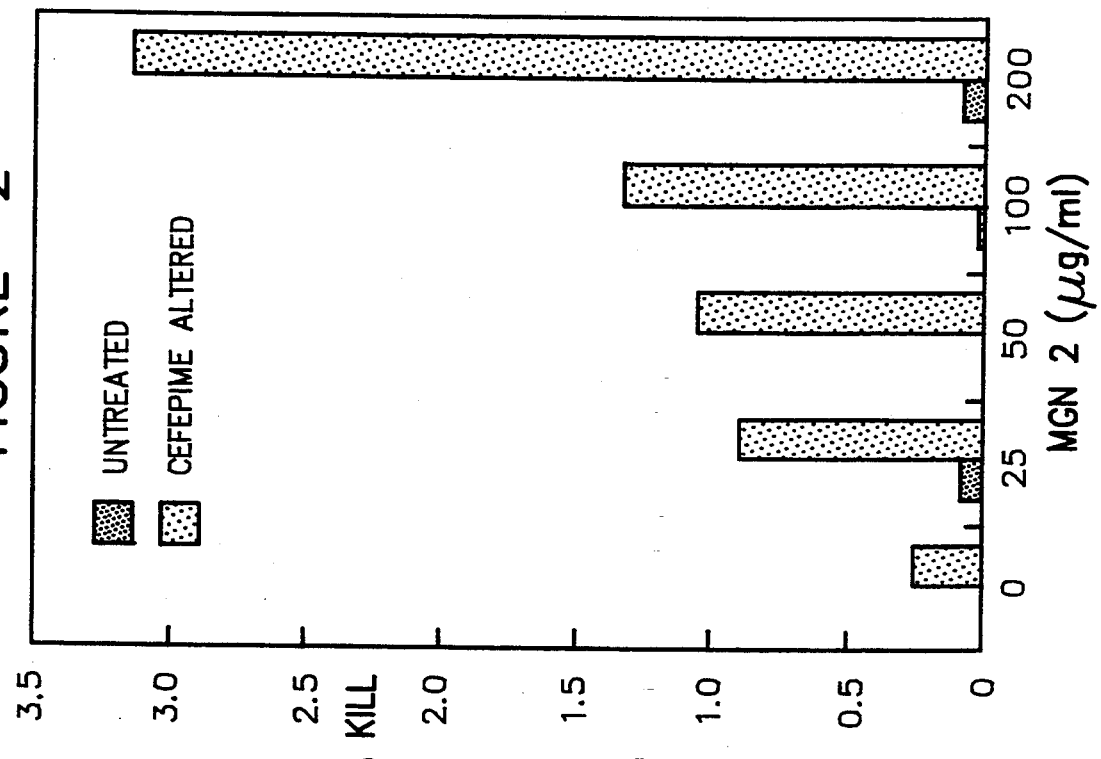
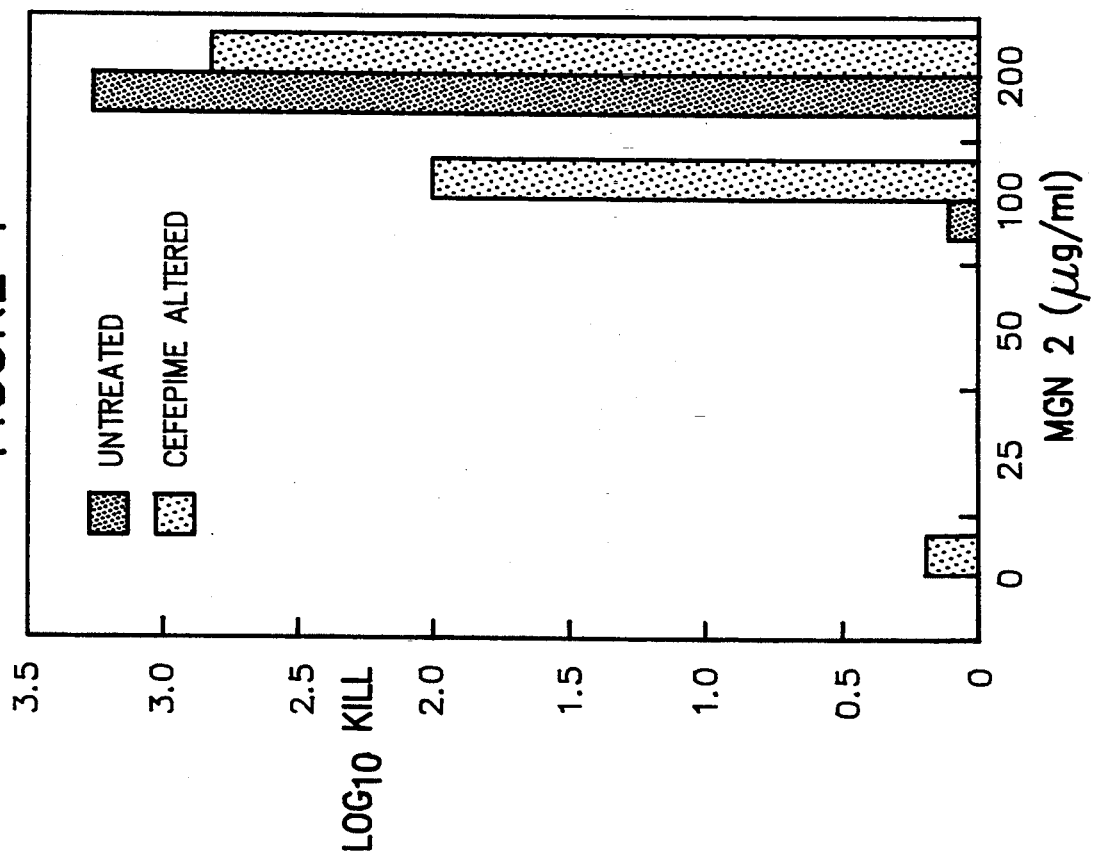

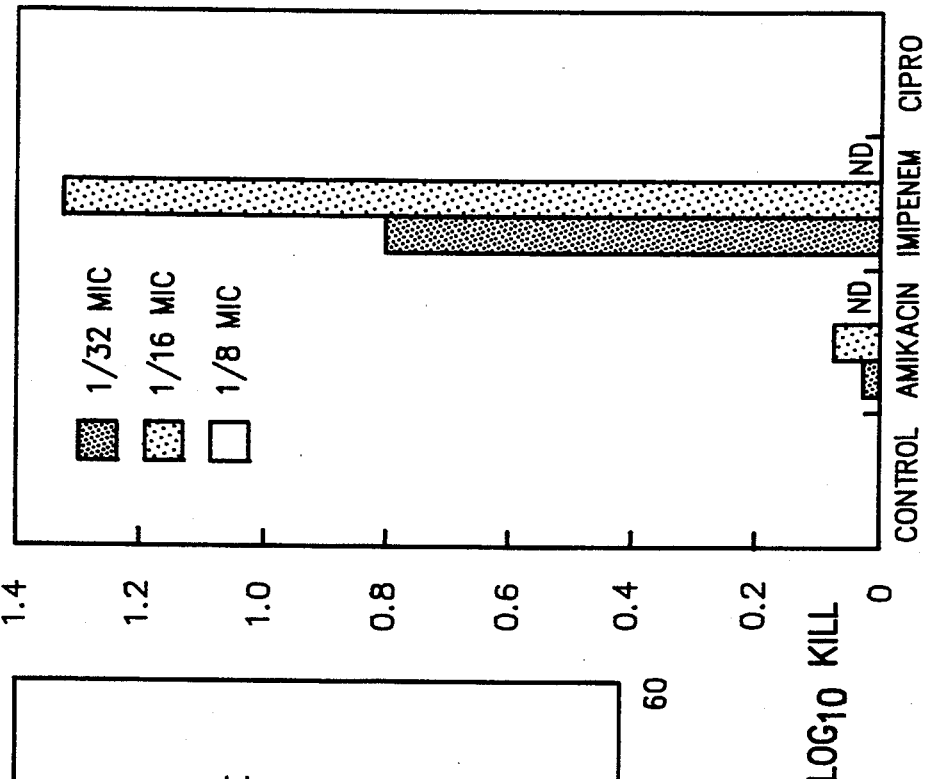
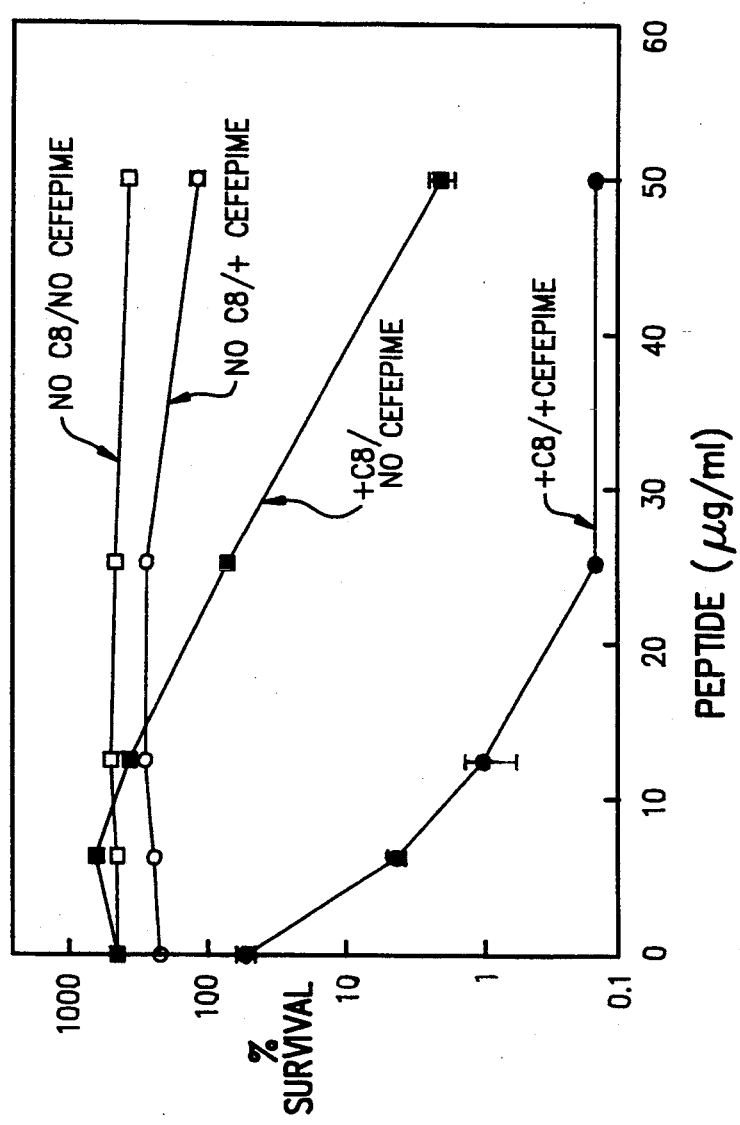

COMPOSITIONS AND METHODS FOR TREATING INFECTIONS CAUSED BY ORGANISMS SENSITIVE TO BETA-LACTAM ANTIBIOTICS

This is a continuation of application Ser. No. 07/655,321, filed Feb. 19, 1991 and now abandoned which is a continuation-in-part of application Ser. No. 07/484,020 filed Feb. 23, 1990, and now abandoned.

TABLE OF CONTENTS

1. Field of the Invention . . .
2. Background of the Invention . . .
  2.1. β-Lactam Antibiotics . . .
  2.2. Cationic Oligopeptides . . .
  2.3. Effects of Serum on Bacterial Growth . . .
  2.4. In Vitro Selection Methods for Compositions Having Bactericidal Activity . . .
3. Summary of the Invention . . .
4. Brief Description of the Figures . . .
5. Detailed Description of the Invention . . .
  5.1 Compositions for Treating Infections Caused by an Organism Susceptible to a β-Lactam Antibiotic . . .
  5.2. Applications and Methods of Use . . .
  5.3. In Vitro Methods of Screening for Compositions Synergistic with β-Lactam Antibiotics . . .
6. Example: Synergistic Action of Cephalosporins and the Cationic Peptide Magainin 2 . . .
  6.1. Materials and Methods . . .
    6.1.1. Reagents and Buffers . . .
    6.1.2. Bacterial Strains and Culture Conditions . . .
    6.1.3. Serum . . .
    6.1.4. Determination of the Minimal Inhibitory Concentration (MIC) . . .
    6.1.5. Serum Bactericidal Assay . . .
  6.2. Results . . .
7. Example: Synergistic Action of Cephalosporins and the Cationic Peptide C-13 of Human Platelet Factor-4 . . .
  7.1. Materials and Methods . . .
    7.1.1. Reagents and Buffers . . .
    7.1.2. Bacterial Strains and Culture Conditions . . .
    7.1.3. Serum . . .
    7.1.4. Determination of the Minimal Inhibitory Concentration (MIC) . . .
    7.1.5. Serum Bactericidal Assay . . .
  7.2. Results . . .
8. Example: In Vivo Protective Effect of Magainin and cefepime Combinations . . .
  8.1. Materials and Methods . . .
    8.1.1. Reagents and Buffers . . .
    8.1.2. Bacterial Strains and Culture Conditions . . .
    8.1.3. In Vivo Experiments . . .
  8.2. Results . . .
9. Example: Synthesis of Analogs of C-13 Peptide . .
  9.1. Materials and Methods . . .
    9.1.1. Reagents and Methods . . .
10. Example: In Vitro Screening of C-13 Peptide Analogs by Bacterial Activity and Hemolytic Activity . . .
  10.1 Materials and Methods . . .
    10.1.1. Reagents and Buffers . . .
    10.1.2. Bacterial Strains and Culture Conditions . .
    10.1.3. Serum Bactericidal Assay . . .
    10.1.4. Hemolytic Assay . . .
  10.2. Results . . .
11. Example: In Vivo Protective Effect of C-13 Peptide Analogs and cefepime Combinations . . .
  11.1. Materials and Methods . . .
    11.1.1. Reagents and Buffers . . .
    11.1.2. Bacterial Strains and Culture Conditions . .
    11.1.3. In Vivo Experiments . . .
  11.2. Results . . .

1. Field of the Invention

The invention is directed to compositions comprising at least two components which act in a synergistic fashion in vivo and are effective in the treatment of an infection caused by an organism susceptible to a β-lactam antibiotic. The invention further includes methods for treating such an infection in a patient by administering effective amounts of such compositions, and to in vitro methods for screening compositions for bactericidal activity in the presence of active complement.

2. Background of the Invention

Bacterial infections remain a major cause of death in critically ill patients, primarily from gram-negative bacterial infections (Klatersky et al., 1988, Eur. J. Cancer Clinical Oncology, 2451:535–545). Infections occurring in such patients progress rapidly and are often fatal.

Patients undergoing chemotherapy often have a low granulocyte count, i.e granulocytopenia, and are particularly predisposed to bacterial infection (Klatersky, 1986, Am. J. Med. 80:2–12). The most common infectious organisms in these patients are the gram-negative bacilli Escherichia coli (*E. coli*), Pseudomonas aeruginosa (*P. aeruginosa*), and Klebsiella pneumoniae (*K. pneumoniae*) and the gram-positive cocci Staphylococcus aureus (*S. aureus*) and Staphylococcus epidermis (*S. epidermis*).

Other patients that are particularly susceptible to both gram-negative and gram-positive bacterial infection are those patients who have tindergone gastrointestinal surgery (Bergamini and Polk, 1989, J. Antimicrobial Chemotherapy 23:301–303), although other surgical patients are also at risk. Currently, antibiotics are the only effective therapy for these patients.

2.1. β-LACTAM ANTIBIOTICS

One group of antibiotics that has been effective in treatment of these patients is the β-lactam antibiotics, which inhibit bacterial cell wall synthesis. A common characteristic of β-lactam antibiotics is their ability to kill a wide variety of different bacteria. This is an important characteristic since it is often not practical to determine the specific bacteria which are causing the disease. In addition, treatment with the antibiotic most often begins before the diagnosis of the infectious organism is made since bacterial infections in these patients can be rapidly fatal. Examples of β-lactam antibiotics include penicillins, cephalosporins, cephamycins, monobactams, pyrazidons, penems, and carbapenems. It has been observed that low concentrations of penicillins induced filamentation of *E. coli*, with bulge formation and lysis occurring only at higher antibiotic concentrations (reviewed in Waxman and Strominger, 1983, Annual Rev. Biochem. 52:825–869). It has also been shown that peptidoglycan transpeptidases are the targets of β-lactam antibiotics and that a multiplicity of proteins in the bacterial cell membrane bind penicillins and related β-lactam antibiotics covalently.

Penicillin G has been effective in inhibiting such gram-positive coccal species as pneumococci and streptococci and gram-negative cocci such as *Neisseria meningitidis* (Neu, 1987, Medical Clinics of North America 71:1051-1064). Initially, aminopenicillins such as ampicillin and amoxicillin were used extensively for therapy of infections caused by *Hemophilus influenzae* (*H. influenzae*), *E. coli*, Salmonella and Shigella. However, an increasing prevalence of plasmid-mediated beta-lactamases in these organisms has been observed. Cephalosporins have been shown to have activity against *Pseudomonas aeruginosa*, meningitis caused by common pathogens, and infections resulting from multiresistant microorganisms, although resistance to these agents is also rising. Another group of β-lactams include carbapenem agents, such as imipenem, which inhibit aerobic and anaerobic gram-positive and gram-negative bacteria. Carbapenems are noted for high affinity for penicillin-binding proteins.

Due to the increasing amount of resistance to β-lactam antibiotics, different combinations of antibiotics have also been administered to these patients. Aminopenicillins have been combined with clavulanate, a beta-lactamase inhibitor to overcome plasmid-mediated β-lactamase present in *H. influenzae*, *E. coli*, Salmonella, and Shigella (Neu, 1987, Medical Clinics of North America 71:1051-1064). β-lactams have also been combined with aminoglycosides (Klastersky, 1986, Am. J. Med. 80:2-13). Such a combination has been found to be somewhat effective, the effectiveness varying with the type of bacteria the combination is used against. It has been found that a combination of β-lactams with other antibiotics may result in antagonism between the two compounds.

An increasing number of reports indicate that antibiotics can affect bacteria in ways other than the expected bactericidal action (Darveau et al., 1990, J. Infect. Dis. 162:914-921, Essig et al., 1982, Arch. Microbiol. 132:245-250; Kadurugamuwa et al., 1988, Antimicrob. Agents and Chemother. 32:364-368; Leying et al., 1986, Antimicrob. Agents and Chemother. 30:475-480; Raponi et al., 1989, Antimicro. Chemother. 23:565-576; Sauerbaum et al., 1987, Antimicrob. Agents and Chemother. 31:1106-1110; Taylor et al., 1981, Antimicrob. Agents and Chemother. 19:786-788; Taylor et al., 1982, Drugs Exptl. Clin. Res. 8:625-631 and Veringa et al., 1988, Drugs Exptl. Clin. Res. 14:1-8). Examples of some of these effects include inhibition of exoenzyme production (Grimwood et al., 1989, Antimicrob. Agents and Chemother. 33:41-47), changes in peptidoglycan structure (Garcia-Bustos and Dougherty, 1987, Antimicrob. Agents and Chemother. 31:178-182), and loss of invasive adhesive properties (Schifferli and Beachey, 1988, Antimicrob. Agents and Chemother. 32:1603-1608 and Vosbeck et al., 1979, Rev. Inf. Dis. 1:845-85 1). These effects are usually observed when bacteria are incubated with antibiotics at levels below the minimal inhibitory concentration (MIC). Effects of subinhibitory concentrations of antibiotics may aid the host in eradicating the bacteria. This is especially relevant with β-lactam antibiotics where it is known that it takes a relatively long time for the bactericidal action of the antibiotic to be manifested.

Generally, antibiotics are dosed to give supra MIC levels throughout therapy. However, since both host and bacterial factors such β-lactamases can influence the amount of active antibiotic at the infection site, supra MIC dosing does not insure adequate antibiotic concentrations for every organism.

2.2. CATIONIC OLIGO PEPTIDES

A variety of cationic oligopeptides having antimicrobial activity have been isolated from human and animal sources. These include magainins (Zasloff et al., 1987, Proc. Natl. Acad. Sci. U.S.A. 84:5449-5453; Zasloff et al., 1988, Proc. Natl. Acad. Sci. U.S.A. 85:910-913; and Zasloff, 1989, U.S. Pat. No. 4,810,777); cecropins (Christensen et al., 1988, Proc. Natl. Acad. Sci. U.S.A. 85:5072-5076 and Stein et al., 1981, Nature (London) 292:246-248); sarcotoxins (Nakajima et al., 1987, J. Biol. Chem. 262:1665-1669 and Okada and Natori, 1985, Biochem. J. 229:453-458); and defensins (Selsted et al., 1985, J. Clin. Investig. 76:1436-1439 and Lehrer et al., U.S. Pat. Nos. 4,543,252; 4,659,692 and 4,705,777).

Magainins have been found in secretions from the skin of *Xenopus laevis*, the South African clawed toad. Two types of magainins have been isolated, magainin 1 and magainin 2 (Zasloff et al., 1987, Proc. Natl. Acad. Sci. U.S.A. 84:5449-5453). Magainin 1 and magainin 2 are closely related to one another, are each 23 amino acids in length, and differ by just two amino acid substitutions. These peptides are water soluble, nonhemolytic at their effective antimicrobial concentrations, and potentially amphiphilic. The effective antimicrobial concentration of magainin needed for activity in a non-serum containing medium or buffer has been found to be a function of the magainin and the microbe treated.

The antimicrobial activity of various synthetic magainin analogs has also been studied (Cuervo et al., 1988, Peptide Research 81:81-86; Zasloff et al., 1988, Proc. Natl. Acad. Sci. U.S.A. 85:910-913; and Chen et al., 1988, Antimicrobial Peptides and Process for Making the Same, U.S. patent application Ser. No. 7-280,363 National Technical Information Service). It was found that removal of the three N-terminal amino acids from magainin-2 did not affect antimicrobial activity (Zasloff et al, 1988, Proc. Natl. Acad. Sci. U.S.A. 85:910-913). However, removal of a fourth amino acid decreased antimicrobial activity significantly. The entire N-terminal region was found to be necessary in magainin 1 (Cuervo et al., 1988, Peptide Research 1:81-86). However, analogs with omissions in the C-terminal region, especially residues alanine-15, glycine-18, or glutamic acid-19 while having equal or increased antimicrobial activity relative to the original magainin 1 or magainin 2 forms, had variable hemolytic action (Cuervo et al., 1988, Peptide Research 1:81-86). Analogs of magainin peptides in which amino acid residues having a low propensity for helical formation are substituted with amino acid residues having a high propensity for helical formation so as to lower susceptibility to exopeptidase action and enhance amphiphilic structural characteristics and antimicrobial properties have been disclosed (Chen et al., 1988, Antimicrobial Peptides and Processes for Making the Same, U.S. patent application Ser. No. 7-280,363 National Technical Information Service).

Two groups of cationic oligopeptides have been isolated from insects, cecropins and sarcotoxins. Cecropins have been isolated from a variety of insect species (Christensen et al., 1988, Proc. Natl. Acad. Sci. U.S.A. 85:5072-5076 and Stein et al., 1981, Nature (London) 292:246-248). Three principal cecropins have been isolated, cecropin A, B, and D having 37, 36, and 36 residues respectively, each having an amphipathic character. It has been found that the N-terminal region is needed for the resulting membrane-disrupting activity of this peptide. Three sarcotoxins have been found to be induced in the hemolymph of *Sarcophaga peregrina*.

Cationic oligopeptides having antimicrobial activity have also been isolated from humans and are known as defensins (Selsted et al., 1985, J. Clin. Investig. 76:1436-1439 and Lehrer et al., U.S. Pat. Nos. 4,543,252; 4,659,692 and 4,705,777). Such peptides are found in macrophages and granulocytes and have high cysteine and arginine content. Six such proteins have been identified.

Peptide fragments of mitochondrial protein precursors have also been shown to be active against gram-positive bacteria (Lee et al., 1986, Biochem. Biophys. Acta. 862:211-219). The CD spectra of these peptides in the presence of phospholipid liposomes demonstrated that antimicrobial activity was generally in parallel with the content of the α-helical amphiphilicity.

The antimicrobial cationic oligopeptides examined to date exhibit certain common characteristics. Fundamentally, they are cationic peptides which kill a wide variety of bacteria as determined by standard in vitro assays. There is strong evidence that their mechanism of action is by insertion into the bacterial inner membrane forming a small hole that allows passage of small ions (Christensen et al., 1988, Proc. Natl. Acad. Sci. U.S.A. 85:5072-5076; Nakajima et al., 1987, J. Biol. Chem. 262:1665-1669; Okada and Natori, 1985, Biochem. J. 229:453-458; and Westerhoff et al., 1989, Biochem. Biophys. Acta. 975:361-369). This ionophore activity blocks the generation of ATP by inhibiting the formation of a proton gradient which is essential for oxidative phosphorylation (Okada and Natori, 1985, Biochem, J. 229:453-458; and Westerhoff et al., 1989, Proc. Natl. Acad. Sci. U.S.A. 86:6597-6601). Consistent with this mechanism of action, several of these peptides have been shown to possess an alpha helical structure in organic solvents (Lehrer et al, U.S. Pat. Nos. 4,543,252; 4,659,692 and 4,705,777; Westerhoff et al., 1989, Proc. Natl. Acad. Sci. U.S.A. 86:6597-6601; and Marion et al., 1988, FEBS Letters 227:21-26) and to form holes in artificial membrane systems (Christensen et al, 1988, Proc. Natl. Acad. Sci. U.S.A. 85:5072-5076 and Cruciani et al., 1988, Biophysical J. 53:9a).

In order for magainins or similar compounds to be therapeutically useful for treatment of bacterial infections that can lead to bacteremia, they must be able to exert their bactericidal action in the presence of human serum. This presents a formidable problem since it has been shown that the activity of at least one human defensin is completely inactivated by human serum (Daher et al., 1986, J. Virol 60:1068-1074).

2.3. EFFECTS OF SERUM ON BACTERIAL GROWTH

A large number of bacteria, especially gram-negative bacteria are killed by fresh serum (Feingold, 1969, J. Infectious Dis. 120:437-444). Two major pathways of complement activation are recognized (reviewed in Joiner et al., 1984, Ann. Rev. Immunol. 2:461-491). The classical pathway is generally activated by the interaction of antibody with an antigenic surface. The first step of activation involves binding of the complement protein C1 to the Fc region of the antigen-bound antibody with subsequent activation of the C1 molecule. Subsequent steps in the classical pathway involve the use of all the complement proteins, C1-C9. The second pathway, the alternative pathway, is activated by binding of other serum proteins to bacteria and subsequent activation of complement protein C3. This pathway then is similar to the classical pathway to the C9 complement protein.

Bacterial killing by the terminal components of complement C5b-9 in the absence of earlier components has been observed. Nearly 3 log killing of deep rough *Salmonella minnesota* (*S. minnesota*) Re 595 and 1 log killing of rough *E. coli* J5 was observed using purified complement components C5, C6, C7, C8, and C9 (reviewed in Joiner et al., 1984, Ann. Rev. Immunol. 2:461-491). It has been demonstrated that complement-mediated membrane damage and cytolysis is effected by the self assembly on target membranes of the C5b-9 complexes, which is amphiphilic and tubular (Podack and Tschopp, 1984, Mol. Immunol. 21:589-603). It appears that C5b-9 generates functional pores across the outer and inner bacterial membrane (Born and Bhadki, 1986, Immunology 59:139-145). The generated transmural pores or channels permit rapid $K^+$ efflux resulting in cell death through the collapse of membrane potential.

2.4. IN VITRO SELECTION METHODS FOR COMPOSITIONS HAVING BACTERICIDAL ACTIVITY

Potential bactericidal compositions are routinely screened by standard in vitro methods. These methods are similar to those described in the Manual of Clinical Microbiology, Fourth Edition, Lennette, E. H., Ed. in Chief, American Society for Microbiology, 1985 pps. 959-987. The only modifications being in certain preferences for media, buffer preparation, etc. Selection of an appropriate antimicrobial agent to treat an infection involves a number of considerations. These include among many: (1) in vitro susceptibility of other target organisms and (2) the relationship of the susceptibility of the target strain to that of other members of the same species. The concentration of a potential antibacterial agent needed to inhibit or kill organisms in vitro and those attained in body fluids during in vivo treatment are subject to direct measurement in the laboratory.

Standard susceptibility test methods include disk diffusion, liquid dilution, and agar dilution. Each of the three methods listed above do not include components which comprise an active complement cascade. Therefore, bactericidal activity only relates to the ability of the antibacterial agent to kill the target organism itself. It has been discovered that certain peptides with in vitro bactericidal activity fail when tested in in vitro assays which include human sera and also fail in vivo. Magainins are an example of this phenomena. Further, any composition which may have no bactericidal or limited bactericidal activity alone but enhances the ability of serum complement to kill bacteria would be missed.

3. SUMMARY OF THE INVENTION

The invention is directed to compositions and methods for treating an infection caused by an organism susceptible to a β-lactam antibiotic. The organism can be a gram-negative or gram-positive bacterium. A composition of the present invention contains at least two components which act in a synergistic fashion in vivo. One of the components of the composition of the present invention is a/β-lactam antibiotic. The β-lactam antibiotic can be a penicillin, a cephalosporin, a carabapenem, a monobactam, a cephamycin, a pyrazidon or a penem. More specifically the cephalosporin is cefepime, cefotaxime or ceftazidime, the carbapenem is imipenem and the monobactam is aztreonam.

The second component of a composition of the present invention is a cationic oligopeptide. Cationic oligopeptides used in combination with β-lactam antibiotic to provide synergistic compositions include magainins, cecropins, sarcotoxins, mitochondrial precursor proteins, and fragments, analogs and derivatives of these peptides. Additional cationic peptides include human platelet factor-4 (PF-4) and fragments, analogs and derivatives thereof, including a C-13 fragment of PF-4. Further, the cationic oligopeptides form an amphipathic alpha helix in the presence of a lipid/aqueous interface. The oligopeptides more particularly are at least 8 to 11 amino acids in length and may generally have an amino acid residue sequence:

$aa_1$-Leu-Tyr-Lys-Lys-$aa_2$-$aa_2$-Lys-Lys-Leu-Leu-$aa_3$-$aa_4$-X;

wherein $aa_1$ is Pro, Ala or Lys, $aa_2$ is Ile or Leu, $aa_3$ is Glu or Lys, $aa_4$ is Ser, Leu or Lys and X is a five amino acid sequence being alpha helical in nature, and having the general sequence of $aa_5$-Lys-Lys-$aa_6$-Gly, wherein $aa_5$ is Ala or Leu and $aa_6$ is Leu or Phe.

Illustrative cationic oligopeptides can be:
Ala-Leu-Tyr-Lys-Lys-Ile-Ile-Lys-Lys-Leu-Leu-Glu-Ser-Ala-Lys-Lys-Leu-Gly (Seq. I.D. #5);
Ala-Leu-Tyr-Lys-Lys-Leu-Leu-Lys-Lys-Leu-Leu-Glu-Ser-Ala-Lys-Lys-Leu-Gly (Sequence I.D. #6);
Ala-Leu-Tyr-Lys-Lys-Leu-Leu-Lys-Lys-Leu-Leu-Lys-Ser-Ala-Lys-Lys-Leu-Gly (Seq. I.D. #7);
Ala-Leu-Tyr-Orn-Orn-Leu-Leu-Orn-Orn-Leu-Leu-Orn-Ser-Ala-Orn-Orn-Leu-Gly
Ala-Leu-Tyr-Lys-Lys-Leu-Leu-Lys-Lys-Leu-Leu-Lys-Lys-Ala-Lys-Lys-Leu-Gly (Seq. I.D. #8);
Ala-Leu-Tyr-Lys-Lys-Leu-Leu-Lys-Lys-Leu-Leu-Lys-Phe-Ala-Lys-Lys-Phe-Gly (Seq. I.D. #10);
Lys-Trp-Lys-Leu-Tyr-Lys-Lys-Leu-Leu-Lys-Lys-Leu-Leu-Lys-Ser-Ala-Lys-Lys-Leu-Gly (Seq. I.D. #11); and
Ala-Lys-Lys-Leu-Leu-Ala-Lys-Leu-Tyr-Lys-Lys-Leu-Leu-Lys-Lys-Leu-Leu-Lys-Ser-Ala-Lys-Lys-Leu-Gly (Seq. I.D. #12).

A cationic oligopeptide can also include:
Ala-Leu-Tyr-Lys-Lys-Leu-Leu-Lys-Lys-Leu-Leu-Lys-Ser-Ala-Lys-Lys-Leu-Gly and the like,
wherein the amino acid residues can be d-amino acids.

The present invention further provides compositions to treat an infection caused by Enterobacteriaceae bacteria, particularly *Escherichia coli*, *Enterobacter clocae* and *Klebsiella pneumoniae*. Compositions of the present invention are also effective in treating infections caused by *Pseudomonas aeruginosa*. The compositions combine β-lactam antibiotics as described above with a membrane active substance. Membrane active substances disrupt essential membrane functions which rely on, for example, the proton motive force including oxidative phosphorylation, essential transport, etc. Membrane active substances include the cationic oligopeptides as described above and hereinbelow.

Methods are also provided to treat infections caused by an organism susceptible to a β-lactam antibiotic. Some of the infections responsive to treatment by the compositions of the present invention are caused by Enterobacteriacaea bacteria, particularly *E. coli*. In the clinical methods therapeutically effective amounts of the compositions of the present invention are administered to patients for a time period sufficient to inhibit the growth of the bacteria. Specific combinations for treatment of bacterial infections caused by *Escherichia coli* include cefepime combined with magainin 2, C-13 peptide of platelet factor-4 and cationic peptides having the amino acid residue sequences:
Ala-Leu-Tyr-Lys-Lys-Leu-Leu-Lys-Lys-Leu-Leu-Glu-Ser-Ala-Lys-Lys-Leu-Gly (Sequence I.D. #6);
Ala-Leu-Tyr-Lys-Lys-Leu-Leu-Lys-Lys-Leu-Leu-Lys-Ser-Ala-Lys-Lys-Leu-Gly (Seq. I.D. #7);
Ala-Leu-Tyr-Orn-Orn-Leu-Leu-Orn-Orn-Leu-Leu-Orn-Ser-Ala-Orn-Orn-Leu-Gly;
dAla-dLeu-dTyr-dLys-dLys-dLeu-dLeu-dLys-dLys-dLeu-dLeu-dLys-dSer-dAla-dLys-dLys-dLeu-Gly.

The present invention further provides in vitro methods to screen compositions for antibacterial activity with complment. Compositions to be tested are combined with a target bacteria and active complement cascade components in a standard medium and after a sufficient time period the antibacterial activity is determined. The active complement components can be added as serum or the components of the complement cascade can be added individually. Human serum is particularly preferred.

Still further advantages and benefits of the present invention will become apparent to those skilled in the art in the following detailed description, examples and claims.

4. BRIEF DESCRIPTION OF THE FIGURES

In the drawings:

FIG. 1 illustrates magainin 2 killing of untreated and cefepime altered *E. coli* in buffer. *E. coli* ATCC 25922 were grown to mid log phase with (cefepime altered) and without (untreated) ¼ MIC cefepime (0.016 μg/ml cefepime). Cells were diluted as described in Section 6.1.5 and added to tubes containing GVB++ buffer, with or without cefepime, and varying concentrations of magainin 2 peptide (indicated on the X axis). Cefepime was present in tubes used to examine cells pregrown with this antibiotic. After 180 minutes at 37° C., bacterial survival was determined by measuring the number of colony forming units (cfu) in each tube. Bacterial counts were determined in triplicate. For each magainin concentration: Log Kill = $\log_{10}$ cfu no magainin − $\log_{10}$ cfu containing magainin.

FIG. 2 illustrates magainin 2 killing of untreated and cefepime altered *E. coli* in human serum. Cells prepared as described in FIG. 1 were added to tubes containing 40% human serum. After 180 minutes at 37° C., bacterial survival was determined by measuring the number of colony forming units (cfu) in each tube. Assays were performed in triplicate. For each magainin concentration: $\log_{10}$Kill = $\log_{10}$ cfu no magainin − $\log_{10}$ cfu containing magainin.

Figure 3:
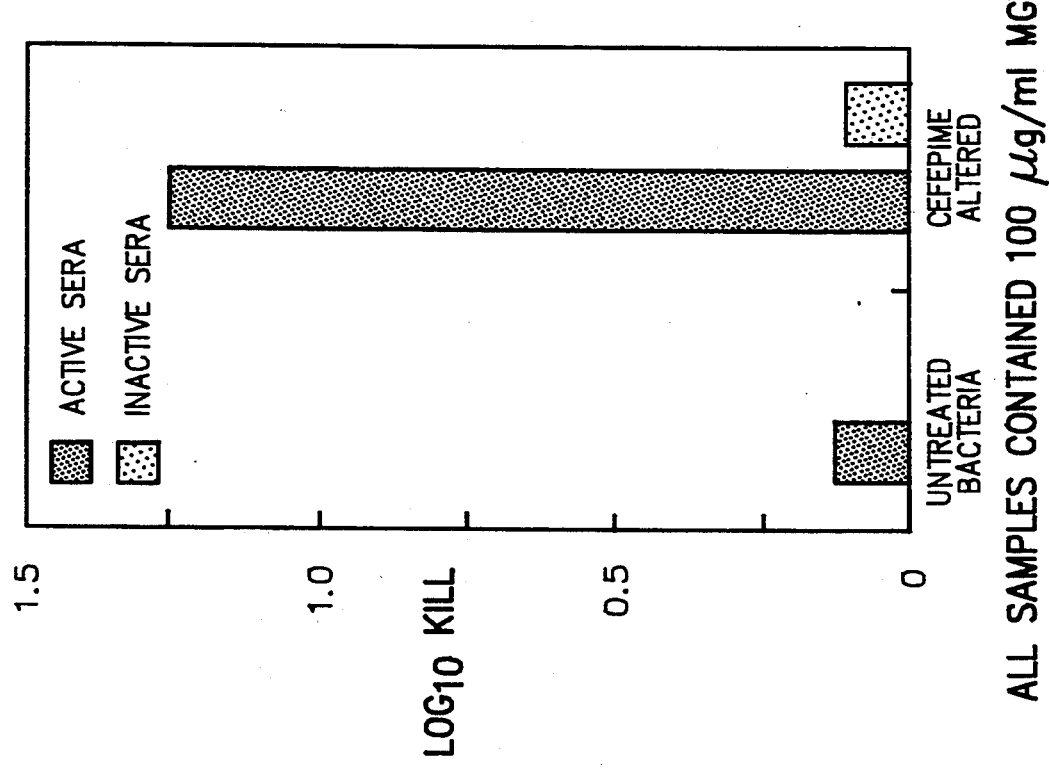

FIG. 3 illustrates magainin 2 killing of *E. coli* in active and heat inactivated serum. Cells prepared as described in FIG. 1 were added to a set of tubes that contained 40% human serum or 40% heat inactivated serum. Cefepime was present in those tubes used to examine cells pregrown with this antibiotic. Tubes also contained either 100 μg/ml magainin 2 or no magainin addition. $\log_{10}$ Kill was calculated for both untreated and cefepime altered bacteria in both active or heat-inactivated serum by the following formula: $\log_{10}$Kill- =Log$_{10}$ cfu no maganinin−Log$_{10}$ cfu containing magainin.

FIG. 4 illustrates inactive sera inhibition of magainin killing of cefepime altered bacteria. Cells were pregrown in cefepime as described in the legend to FIG. 1. Cells were added to a set of tubes that contained cefepime with either 0, 2.5, 5, 10, 20, or 40% heat-inactivated serum. Another set of tubes with identical amounts of heat-inactivated serum contained 200 μg/ml magainin 2. The percent inhibition for each concentration of heat-inactivated serum=(cfu containing magainin/cfu containing no magainin)×100.

FIG. 5 illustrates the role of human complement in magainin killing of untreated and cefepime altered $E.$ $coli.$ $E.$ $coli$ ATCC 25922 were grown with and without ¼ MIC cefepime. Cells were added to a set of tubes that contained either 40% human sera specifically depleted in human complement C8 (no C8) or 40% human sera depleted in C8 to which purified C8 was added back to 50 μg/ml(+C8). Cefepime, when present was added to 0.016 μg/ml (+cefepime). Each set of tubes also contained either 0, 6.25, 12.5, 25, and 50 mg/ml magainin 2. Viable counts were determined at the time of bacterial addition to serum (input) and the percent survival was determined after three hours. The assay was performed in triplicate, the mean±/-1 intra assay standard deviation are shown.

FIG. 6 illustrates the effect of different antibiotics on magainin killing in pooled normal human sera. $E.$ $coli$ ATCC 25922 were pregrown and assays were performed with no antibiotic and at 1/32, 1/16 and ¼ MIC for each antibiotic examined. Bacteria were added to two sets of tubes both containing 40% pooled normal human serum and either 200 μg/ml magainin 2 or no magainin. For each antibiotic concentration: Log$_{10}$Kill=Log$_{10}$ cfu no magainin−Log$_{10}$ cfu containing magainin. Cipro=ciprofloxacin, ND=not determined.

Figure 8:
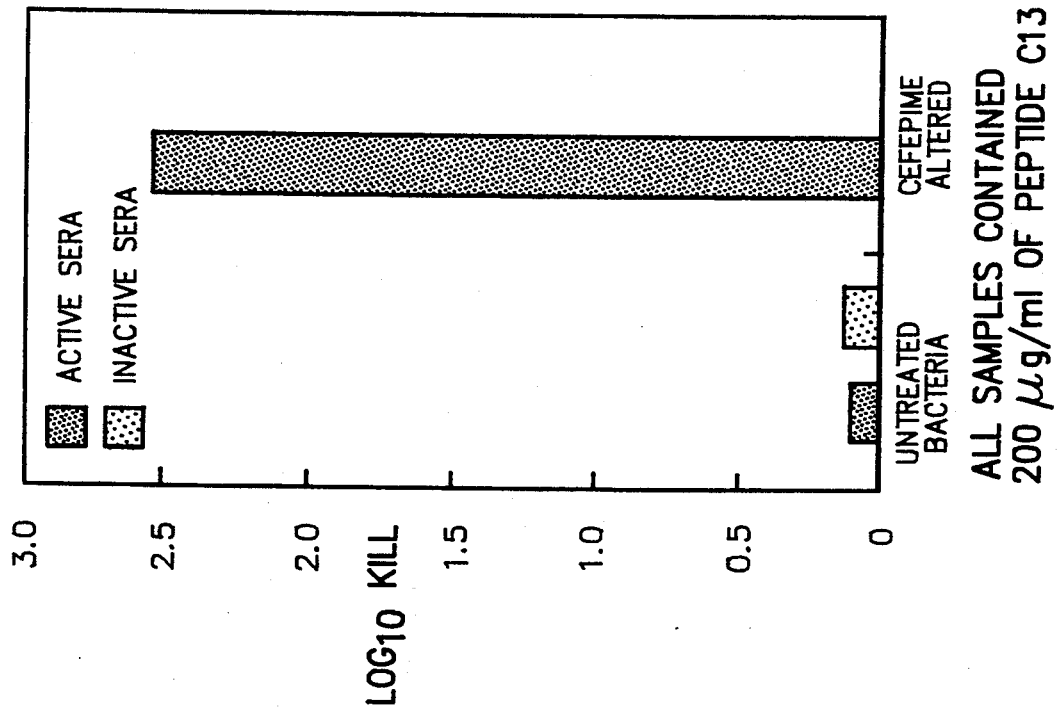
Figure 7:
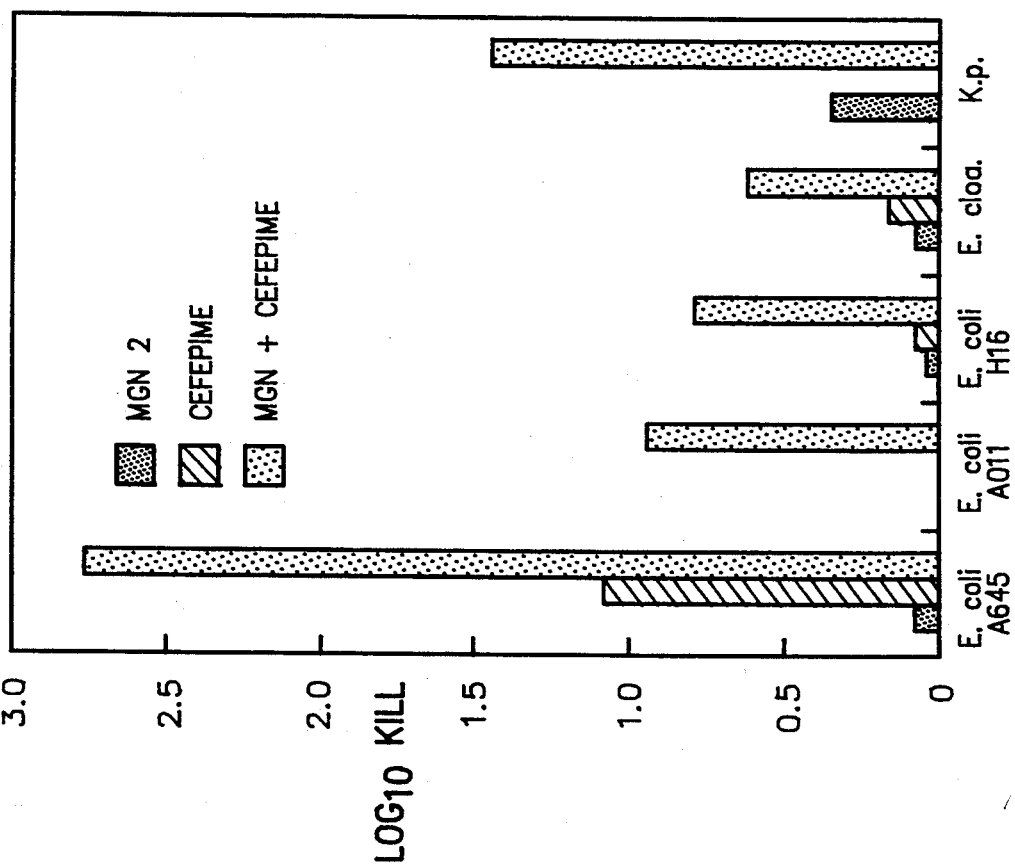

FIG. 7 illustrates the amount of magainin/cefepime killing against a variety of bacteria. Bacterial cells were grown to mid log phase with and without ¼ MIC cefepime. Bacteria were added to two sets of tubes both containing 40% pooled normal human serum and either 200 μg/ml magainin 2 or no magainin. In addition, cefepime was present in tubes used to examine cells pregrown with this antibiotic. For each bacterial strain, the Log$_{10}$Kill was calculated as follows: MGN 2=Log$_{10}$kill no MGN−Log$_{10}$kill+MGN; cefepime=-Log$_{10}$kill no MGN−Log$_{10}$kill no MGN+cefepime; MGN+cefepime=Log$_{10}$kill no MGN−Log$_{10}$kill+MGN+cefepime. E. Cloa=$E.$ $cloacae,$ K.p.=$K.$ $pneomoniae.$ FIG. 8 illustrate the C-13 peptide from PF-4 killing of $E.$ $coli$ in active and heat inactivated serum. $E.$ $coli$ ATCC 25922 were grown with and without 1/5 MIC cefepime. Cells were added to a set of tubes that contained 40% pooled normal human serum or 40% heat inactivated serum. Cefepime was present in those tubes used to examine cells pregrown with this antibiotic. Tubes also contained 200 μg/ml C-13 peptide. For untreated and cefepime altered bacteria in active or heat-inactivated serum: Log$_{10}$Kill=Log$_{10}$cfu no C-13−Log$_{10}$cfu+C-13. Note: no killing occurred with cefepime altered bacteria in inactive sera.

5. DETAILED DESCRIPTION OF THE INVENTION

The invention is directed to compositions and methods for treating infections caused by an organism susceptible to a β-lactam antibiotic. Such compositions comprise at least two components which act in a synergistic fashion. As a result, the compositions have greater efficacy in vivo than can be attained with each individual component. Synergism can also be manifested by equal or greater efficacy with lower and/or less frequent doses than would be required for each individual component. The compositions of the invention can also be useful in treating antibiotic resistant strains. Further, the invention is directed to in vitro methods of screening for compositions synergistic with β-lactam antibiotics in bacterial cell killing and for compositions capable of killing bacteria with active complement for bactericidal activity.

5.1 COMPOSITIONS FOR TREATING INFECTIONS CAUSED BY AN ORGANISM SUSCEPTIBLE TO A β-LACTAM ANTIBIOTIC

The invention is directed to a composition comprising at least two or more components for treating an infection caused by an organism susceptible to a β-lactam antibiotic. Organisms susceptible to a β-lactam antibiotic can be gram-positive bacteria (e.g. Streptococcus) or gram-negative bacteria of, for example, the Family Enterobacteriaceae (e.g. *Escherichia coli, Klebseilla pneumoniae* and *Enterobacter cloacae*), the Family Pseudomonadaceae (i.e. *Pseudomonas aeruginosa*), and the Family Bacteroides. In one embodiment, the composition contains: (1) a β-lactam antibiotic which inhibits the growth of the organism and (2) a cationic oligopeptide. The β-lactam antibiotic may inhibit the growth of the bacteria by altering the structure of the bacterial membrane, and the cationic oligopeptide may form channels in the bacterial membrane. Therefore, the β-lactam antibiotic and the cationic oligopeptide can act in a synergistic manner.

β-lactam antibiotics as defined in Section 2.1, supra are those antibiotics which inhibit bacterial cell wall synthesis. Such antibiotics may include, but are not limited to, penicillins, cephalosporins (e.g. cefepime, cefotaxime, and ceftazidime), carbapenems (e.g. imipenim), monobactams (e.g. aztreonam), cephamycins, pyrazidons, and penems. The β-lactam antibiotics may be obtained from commercial sources and by using procedures for obtaining such antibiotics commonly known to those skilled in the art.

The term "cationic oligopeptide" as used in the present specification and the claims refers to amphipathic oligopeptides with antimicrobial activity, which may insert into the bacterial inner membrane and when combined with β-lactam antibiotic in vivo provide synergistic bacterial cell killing.

In one embodiment the cationic oligopeptides contain regions which are α helical in nature when in the presence of a lipid/aqueous interface. The helix formed can be either left or right handed and can contain nonprotein amino acids (i.e., alpha, alpha-dialkyl amino acids, d amino acids, or amino acid derivatives). Further, the cationic oligopeptides form amphipathic helices. Some areas of the linear peptide are of hydrophobic character while others are of hydrophilic character such that when the helix forms one side of the helix is predominately hydrophobic while the other is predominately hydrophilic. Although this characteristic may not be obvious on inspection of the linear sequence, this property may be easily recognized by the use of helical net diagrams (Crick, 1953, Acta Crystallogr. 6:684–697) or axial helical projections (Schiffer et al., 1967, Biophys. J. 7:121–135). The regions of hydrophobic or hydrophilic character are not necessarily made up exclusively of amino acid residues of like character, but need only be predominately hydrophobic or hydrophilic as long as the amphipathic nature of the peptide is retained. It should similarly be noted that regions of similar physical characteristics need not strictly be parallel with the axis of the helix but can be at an oblique angle with the axis. Additionally, the regions of helicity may be broken by non-helical regions and still retain enhanced bactericidal activity in the presence of $\beta$-lactam antibiotics.

In a specific embodiment, the cationic oligopeptide can be human platelet factor-4 and fragments, analogs, and derivatives thereof. Analogs and derivatives are those peptides which maintain the cationic amphipathic $\alpha$ helical nature of the peptide and further retain bactericidal activity. Human platelet factor-4 (PF-4) which comprises 70 amino acids, is a platelet $\alpha$-granule protein which has a high affinity for heparin and inhibits growth factor stimulated endothelial cell proliferation (Maione et al., 1990, Science 247:77–80) and also possesses immunoregulatory activity (Zucker et al., 1989, Proc. Natl. Acad. Sci. U.S.A. 86:7571–7574). It was found that a carboxy terminal fragment 13 amino acids in length (amino acids 58–70), hereinafter referred to as the C-13 PF-4 fragment or C-13 peptide having the sequence, pro-Leu-Tyr-Lys-Lys-Ile-Ile-Lys-Lys-Leu-Leu-Glu-Ser (Seq. I.D. #1)

retained both growth inhibitory and immunoregulatory activity (Maione et al, 1990, Science 247:77–80 and Zucker et al., 1989, Proc. Natl. Acad. Sci. U.S.A. 86:7571–7574). It was found, however, that smaller peptides, C-12 (amino acids 58–69) and C-11 (amino acids 58–68) were less inhibitory (Maione et al., 1990, Science 247:77–80). Little inhibitory action was observed with the C-10 (amino acids 58–67) peptide.

The cationic oligopeptides can be prepared by procedures known to those skilled in the art. In one embodiment, the cationic oligopeptides may be isolated from their natural sources. For example, as disclosed in Section 2.2. supra, magainins may be isolated from *Xenopus laevis* (Zasloff, 1987, Proc. Natl. Acad. Sci. U.S.A. 84:5449–5453), cecropins and sarcotoxins may be isolated from insects (Christensen et al., 1988, Proc. Natl. Acad. Sci. U.S.A. 85:5072–5076 and Nakajima et al., 1987, J. Biol. Chem. 262:1655–1669), mitochondrial precursor proteins may be isolated from mitochondria, and human platelet factor-4 may be isolated from platelets using procedures known in the art. Alternatively, cationic oligopeptides may be obtained by recombinant DNA procedures. Methods have, for example, been disclosed for obtaining magainins (Zasloff, 197, Proc. Natl. Acad. Sci. U.S.A. 84:5449–5453), cecropins (Christensen et at., 1988, Proc. Natl. Acad. Sci. U.S.A. 85:5072–5076), sarcotoxins (Nakajima et al, 1987, J. Biol. Chem. 262: 1665–1669), and human platelet factor-4 (St. Charles et al., 1989, J. Biol. Chem. 264:2092–2099). The cationic oligopeptides of the present invention may also be obtained by chemically synthesizing the oligopeptide sequences using procedures known in the art, such as commercially available peptide synthesizers and the like. Such standard techniques of polypeptide synthesis can be found described in such publications as Merrifield, 1963, J. Chem. Soc. 85:2149–2154 and Hunkapillar et al., 1984, Nature (London) 310:105–111.

Various analogs of the C-13 peptide of human platelet factor-4 have been synthesized. Analogs which retain bactericidal activity, are $\alpha$ helical having approximately 3.6 amino acids per turn, are at least about 11 to 18 amino acids in length, have alternating hydrophobic and hydrophilic regions every two to three amino acid residues and are considered a part of the present invention. Analogs synthesized which disrupt the helical nature of the molecule or the amphipathic nature of the molecule greatly reduce or obviate any bactericidal activity.

Generally, the amino acid sequence of the cationic $\alpha$ helical amphipathic compositions of the present invention having antibacterial activity comprise the amino acid residue sequence:

aa$_1$-Leu-Tyr-Lys-Lys-aa$_2$-aa$_2$-Lys-Lys-Leu-Leu-aa$_3$-aa$_4$-X wherein aa$_1$ is Pro, Ala or Lys; aa$_2$ is Ile or Leu; aa$_3$ is Glu or Lys; aa$_4$ is Ser, Leu or Lys and X is a five amino acid sequence comprising the amino acid sequence Ala-Lys-Lys-Leu-Gly.

Specific embodiments of the present invention include oligopeptides having the following amino acid residue sequences:

Pro-Leu-Tyr-Lys-Lys-Ile-Ile-Lys-Lys-Leu-Leu-Glu-Ser;

Ala-Leu-Tyr-Lys-Lys-Ile-Ile-Lys-Lys-Leu-Leu-Glu-Ser-Ala-Lys-Lys-Leu-Gly;

Ala-Leu-Tyr-Lys-Lys-Leu-Leu-Lys-Lys-Leu-Leu-Glu-Ser-Ala-Lys-Lys-Leu-Gly;

Ala-Leu-Tyr-Lys-Lys-Leu-Leu-Lys-Lys-Leu-Leu-Lys-Ser-Ala-Lys-Lys-Leu-Gly;

dAla-dLeu-dTyr-dLys-dLys-dLeu -dLeu-dLys-dLys-dLeu-dLeu-dLys-dSer-dAla-dLys-dLys-dLeu-Gly;

Ala-Leu-Tyr-Orn-Orn-Leu-Leu-Orn-Orn-Leu-Leu-Orn-Ser-Ala-Orn-Orn-Leu-Gly;

Ala-Leu-Tyr-Lys-Lys-Leu-Leu-Lys-Lys-Leu-Leu-Lys-Lys-Ala-Lys-Lys-Leu-Gly;

Ala-Leu-Tyr-Arg-Arg-Leu-Leu-Arg-Arg-Leu-Leu-Arg-Ser-Ala-Arg-Arg-Leu-Gly;

Ala-Leu-Tyr-Lys-Lys-Leu-Leu-Lys-Lys-Leu-Leu-Lys-Phe-Ala-Lys-Lys-Phe-Gly;

Lys-Trp-Lys-Leu-Tyr-Lys-Lys-Leu-Leu-Lys-Lys-Leu-Leu-Lys-Ser-Ala-Lys-Lys-Leu-Gly; and Ala-Lys-Lys-Leu-Ala-Lys-Leu-Tyr-Lys-Lys-Leu-Leu-Lys-Lys-Leu-Leu-Lys-Ser-Ala-Lys-Lys-Leu-Gly.

Having described the general structure of the cationic $\alpha$ helical amphiphilic bactericidal composition C-13 peptide of platelet factor-4 and various analogs and the derivatives having antibacterial activity, these peptides can be routinely synthesized by standard techniques well known in the art, such as by commercially available peptide synthesizers and the like.

It is noted however, that given the general structure of the antibacterial compositions of the present invention and methods of screening for compositions having synergistic activity with $\beta$-lactam antibiotics or human complement components various other analogs and derivatives can be easily predicted, generated and/or prepared by standard and common methods such as computer modeling and the like. All such analogs and derivatives which are equivalent in structure and function to the compositions described herein are encompassed within the scope of the present disclosure.

In a specific embodiment, the composition comprising: (1) a $\beta$-lactam antibiotic which inhibits the growth of bacteria and (2) a membrane active substance can be used to treat an infection caused by the bacteria. Examples of β-lactam antibiotics are discussed supra. The term "membrane active substance" as used in the present specification and the claims refers to a substance which is capable of interfering with integral membrane functions. Such functions include, but are not limited to, oxidative phosphorylation, essential transport, and other membrane activities associated with the proton motive force. An example of such a substance is a cationic oligopeptide. Illustrative cationic peptides as discussed supra include, but are not limited to, magainins (e.g. magainin 1 and magainin 2), cecropins, sarcotoxins, mitochondrial precursor proteins, human platelet factor-4, and fragments, analogs, and derivatives thereof.

In one very specific embodiment a composition comprising (a) cefepime and (b) magainin 2 may be used to treat infections caused by *Escherichia coli, Pseudomonas aeruginosa, Enterobacter clocae,* and *Klebseilla pneumoniae.* In another specific embodiment, a composition comprising; (a) cefepime and (b) the C-13 peptide of human platelet factor-4 may be used to treat infections caused by *Escherichia coli.* In still another specific embodiment, a composition comprising; (a) cefepime and (b) analogs of the C-13 peptide can be used to treat infections caused by *Escherichia coli.* In other very specific embodiments, a composition comprising: (a) ceftazidime, aztreonam, or imipenem and (b) magainin 2 may be used to treat infections caused by *Escherichia coli.* Compositions comprising: (a) aztreonam and (b) C-13 peptide analog G may be used to treat infections caused by *Escherichia coli* in yet another very specific embodiment.

5.2. APPLICATIONS AND METHODS OF USE

The present invention also relates to methods for treating an infection in a patient caused by an organism susceptible to a β-lactam. In one embodiment of the invention, the method comprises administering to a patient a therapeutically effective amount of a composition comprising (1) a β-lactam antibiotic which inhibits the growth of the organism and (2) a cationic oligopeptide for a time period sufficient to inhibit the bacterial infection. β-lactam antibiotics and cationic oligopeptides are defined and discussed in Section 5.1., supra. In a specific embodiment, the amount of the β-lactam may be a sub-inhibitory dosage.

The invention also relates to a method for specifically treating an infection caused by Enterobacteriaceae bacteria by administrating to a patient a composition which contains an amount of a β-lactam antibiotic which inhibits the growth of the Enterobacteriaceae and at least one membrane active substance. In one embodiment, the amount of the β-lactam antibiotic administered produces a sub-inhibitory concentration of the antibiotic at the infectious site in the patient. The membrane active substance, as discussed in Section 5.1 supra, can include serum and components thereof and cationic oligopeptides.

In a very specific embodiment, an infection caused by *Escherichia coli, Pseudomonas aeruginosa, Enterobacter clocae,* and *Klebsiella pneumoniae* may be treated by administering to a patient an effective amount of a composition which contains: (a) cefepime and (b) magainin 2. In another very specific embodiment, an infection caused by *Escherichia coli* may be treated by administering to a patient an effective amount of a composition containing: (a) cefepime and (b) the C-13 peptide of human platelet factor-4. In other very specific embodiments an infection caused by *Escherichia coli* may be treated with an effective amount of a composition which contains: (a) ceftazidime, aztreonam or imipenem and (b) magainin 2 or with an effective amount of a composition which combines: aztreonam and the C-13 peptide analog G, as herein below described.

The compositions of the present invention may be used to treat a variety of bacterial infections. As discussed in Section 2, supra, several groups of individuals are especially susceptible to bacterial infections. These include critically ill patients, cancer patients undergoing chemotherapy, and surgical patients. Such compositions can be used to effectively treat such individuals.

The compositions of the invention can be formulated for a variety of modes of administration, including systemic and topical or localized administration. According to one embodiment of the present invention, the active agents are mixed together prior to administration. In an alternative embodiment of the method of the invention, the active agents can be administered separately at one time point or at separate times.

Techniques and formulations for administering the compositions of the present invention generally may be found in Remington's Pharmaceutical Sciences, Meade Publishing Co., Easton, Pa., latest edition. For systemic administration, injection is preferred and may be intramuscular, intravenous, intraperitoneal, and subcutaneous. For injection, the compositions of the invention are formulated in liquid solutions, preferably in physiologically compatible buffers, such as Hank's or Ringer's. In addition, the compositions may be formulated in solid form and redissolved or suspended immediately prior to use. Lyophilized forms are also included.

Systemic administration can also be by transmucosal or transdermal means, or the compositions may be administered orally. For transmucosal or transdermal administration, penetrants appropriate to the barrier to be permeated are used in the formulation. Such penetrants are generally known in the art and include, for example, bile salts and fusidic acid derivatives for transmucosal administration. In addition, detergents may be used to facilitate permeation. Transmucosal administration may be through nasal sprays, for example, or by using suppositories. For oral administration, the compositions are formulated into conventional oral administration forms such as capsules, tablets, and tonics.

For topical administration, the compositions of the invention are formulated into ointments, salves, gels, or creams, as generally known in the art.

5.3. IN VITRO METHODS OF SCREENING FOR COMPOSITIONS SYNERGISTIC WITH β-LACTAM ANTIBIOTICS

Further, the present invention relates to improved methods of in vitro screening for compositions with bactericidal activity, particularly cationic α helical amphiphilic peptides. The methods are generally those methods known to one skilled in the art, but further include the components of a functional complement cascade. Prior art methods include disk diffusion, agar dilution, and microdilution and macrodilution broth procedures. Each of these methods can be modified so as to include an active complement cascade. The inclusion of functional complement cascade enables the recognition of certain compositions which require active complement for bactericidal activity. These compositions when used in vivo are combined with complement upon administration as complement is part of the mammalian immune system. Prior art in vitro screening methods which do not include active complement do not recognize these compositions and therefore precluded the discovery of many active novel compositions including those of the present invention.

Active complement components for use in the in vitro screening assays of the present invention can be added in the form of serum. Serum isolated from humans, rats, guinea pigs, rabbits, etc., are known to contain high levels of active complement and can be used in the assays of the present invention. Human complement is preferred. A functional complement cascade can also be provided as its various components and added to standard assay medium.

Having described the present invention and some of its embodiments, the following examples are presented for illustration and not by way of limitation.

6. EXAMPLE: SYNERGISTIC ACTION OF CEPHALOSPORINS AND THE CATIONIC PEPTIDE MAGAININ 2

In the example described herein, the synergistic action of different types of $\beta$-lactam antibiotics and magainin is demonstrated. In these experiments, subinhibitory concentrations of the antibiotic and magainin, when combined, will kill bacteria. When either agent is administered alone, little or no killing results. The second type of synergy applies to the application of these two agents in human serum. In the presence of human serum the magainin/antibiotic combination killed bacteria at lower concentrations than that observed in buffer. These results indicate that these compositions maybe useful for the in vivo treatment of infections caused by bacteria. This represented an additional synergistic effect. The synergy in serum requires a heat labile factor. This factor was identified as serum complement by performing experiments with serum specifically depleted in complement protein C8.

6.1. MATERIALS AND METHODS

6.1.1. REAGENTS AND BUFFERS

The following buffers were used: gelatin-veronal buffer (GVB++) (Gewortz H. et al., 1985, in Manual of Clinical Immunology, N. R. Rose and H. Freedman (eds) ASM, Washington, D.C.). In addition, 0.1% dextrose was added to the buffer as a carbon source. Phosphate buffered saline was prepared in house. Antibiotics were obtained from Dr. Robert Kessler, Bristol-Myers Squibb Company, Wallingford, Conn. in the lyophilized form. Magainin 2 was synthesized in house from the published amino acid sequence (Zasloff et al, 1987, Proc. Natl. Acad. Sci. U.S.A. 84:5479-5483; Zasloff et al., 1988, Proc. Natl. Acad. Sci. U.S.A. 85:910-913; and Zasloff, 1989, U.S. Pat. No. 4,810,777).

6.1.2. BACTERIAL STRAINS AND CULTURE CONDITIONS

*Escherichia coli* ATCC 25922 which was used for most of the experiments was obtained from the American Type Culture Collection (ATCC). Other *E. coli* strains were A011 which was obtained from Harborview Medical Center, Seattle, Wash. and H16 which was obtained from Walter Reed Army Inst. of Research, Dept. of Bacterial Diseases., Washington, D.C. In addition, *Klebsiella pneumoniae* strain ATCC 13883 and an *Enterobacter cloacae* obtained from the Veterans Administration Hospital, Seattle, Wash. were examined. Strains were examined for purity, properly identified, and then stored at $-70°$ C. All strains were grown in AMH (Adjusted Mueller Hinton) (Jones et al., 1985, in Manual of Clinical Microbiology, E. H. Lennette (ed.), ASM, Washington, D.C.).

6.1.3. SERUM

Blood was obtained from five healthy volunteers and was allowed to clot at room temperature for 1 hour. After an additional 20 min incubation at 4° C. the blood was centrifuged for 15 min at 1,500×g. Serum was removed and pooled, ethylene-diaminetetraacetic acid (EDTA, Sigma Chemical Co., St. Louis, Mo.) was added to a concentration of 10 mM and the serum was stored at $-70°$ C. in small amounts as pooled normal human serum (PNHS). Shortly before use the sera was thawed and one part 0.1M $CaCl_2$ to 9 parts serum was added, or alternatively, serum was frozen without the EDTA additive and used without addition of $CaCl_2$. The serum was kept on ice until mixed with bacteria for the serum bactericidal assay. Where indicated, serum complement was inactivated by heating at 56° C. for 30 min.

6.1.4. DETERMINATION OF THE MINIMUM INHIBITORY CONCENTRATION (MIC)

The MIC represents the lowest concentration of antimicrobial agent at which complete inhibition occurs. MIC's were determined by the microdilution plate dilution method using AMH (Manual of Clinical Microbiology, Fourth Edition, Lennette, E. H. Ed. in Chief, ASM. 1985. pps 972-977). At least three different determinations were performed with each antibiotic for each strain.

6.1.5. SERUM BACTERICIDAL ASSAY

Bacteria inoculated from overnight cultures were grown to mid log phase with or without antibiotic (Absorbance at 660 nm between 0.35 and 0.5; approximately $2-3 \times 10^8$ cells/ml for cells grown with cefepime and $9 \times 10^8$ cells/ml for cells grown without cefepime). Cells were diluted without washing to $1 \times 10^4$ cells/ml in gelatin-veronal buffer (GVB++) and 0.05 ml was added to serum in a 1.5 ml Eppendorf vial. Bacterial cells that were pregrown in antibiotic were also diluted in GVB++ containing the same concentration of antibiotic. Either pooled normal human serum (PNHS) or heat inactivated PNHS was prepared beforehand by dilution to the appropriate concentration in 0.2 ml of GVB++. Antibiotics or magainins when present, were added to the serum mixture before the addition of bacteria. The total reaction mixture was 0.25 ml. The number of bacteria added to serum was determined by adding 0.05 ml of the bacterial suspension to a tube containing only GVB++ and plating at the beginning of the assay. The reaction mixtures were then rotated at 37° C. up to three hours. Samples (25 $\mu$l) were removed at intervals for plate count analysis. The number of colony forming units was determined after overnight incubation of trypticase soy agar. Colony forming units were determined in triplicate and the average determined.

6.2. RESULTS

The effect of magainin 2 (MGN 2) and cefepime (a cephalosporin antibiotic) was studied in buffer. As shown in FIG. 1, a combination of cefepime and 100 $\mu$g/ml MGN 2 yielded greater than 1.5 log kill. Less than 0.3 log₁₀kill was observed when cefepime alone was added. Additionally, no significant killing was observed with 100 μg/ml of MGN 2 alone. However, over three logs (99.9%) of bacterial killing was observed when bacteria were incubated with 200 μg/ml of MGN 2. This observation extends the data of Zasloff as it identifies a synergistic combination.

The effect of MGN 2 on untreated bacteria (bacteria not treated with cefepime) and cefepime altered bacteria was also examined in the presence of 40% pooled normal human serum (PNHS) (see FIG. 2). When untreated bacteria were added to serum, no significant MGN killing was observed. This is in stark contrast to the previous observations in buffer where 200 μg/ml MGN 2 completely killed the bacterial strain (compare FIGS. 1 and 2). Clearly then PNHS blocked the action of MGN 2 (and MGN 1, data not shown) when the killing of untreated bacteria was examined. However, when cefepime altered bacteria were examined, MGN killing was enhanced by the presence of the PNHS. MGN killing was observed at 25 μg/ml in PNHS where no killing was observed at this concentration in buffer. Therefore, PNHS blocks the bactericidal activity of MGN 2 on untreated bacteria and enhances MGN bactericidal activity on cefepime altered bacteria.

To determine whether a heat-labile or heat stable factor in PNHS was responsible for the synergy between cefepime and MGN 2, killing in PNHS that was heated to 55° C. for 30 min to inactivate serum complement (inactive serum) and active sera was examined. When examined on untreated bacteria, once again little or no killing was observed with or without 100 μg/ml MGN present (see FIG. 3). When cefepime altered bacteria were examined, heat inactivation of the sera totally abrogated the MGN/cefepime killing observed in active sera (see FIGS. 3 and 4). This experiment clearly demonstrates that when killing in PNHS is examined a heat labile factor in PNHS (probably complement) is required for MGN killing of cefepime altered bacteria.

The nature of the heat labile factor in serum was determined to be serum complement. The ability of magainins to kill cefepime altered and untreated *E. coli* ATCC 25922 was examined in human sera which was specifically depleted in complement protein C8. When this component of the complement cascade was absent from serum, no magainin killing of the bacteria was observed (FIG. 5). However, when purified C8 was added back to physiological concentrations (50 μg/ml), significant killing was observed. In addition, killing of cefepime altered *E. coli* occurred at significantly lower concentrations of magainins than that required for killing of untreated bacteria.

The effects of different antibiotics in pooled normal human serum was also studied. Bacteria were pregrown and assays were performed at 1/32, 1/16, and ⅛ MIC for each antibiotic examined. Bacteria were added to two sets of tubes both containing 40% pooled normal human serum and either 200 μg/ml magainin 2 or no magainin. As shown in FIG. 6, the β-lactam antibiotic, imipenem, was synergistic with magainin 2, but neither Amikacin, an aminoglycoside and ciproflaxacin, a quinoline were synergistic. Additionally, cefepime, aztreonam and ceftazidime, which were all β-lactam type antibiotics, were synergistic with magainins.

The amounts of magainin/cefepime killing against a variety of bacteria was studied. The bacteria studied include E. Coli strain A645; *E. coli* strain A011, *E. coli* strain H16, *E. clocae,* and *K. pneumoniae*. Bacterial cells were grown to mid log phase with and without ¼ MIC cefepime. Bacteria were added to two sets of tubes both containing 40% pooled normal serum and either 200 μg/ml magainin 2 or no magainin.

As shown in FIG. 7, all five bacterial strains showed some synergy with magainins. When MGN is present, there is a significant increase in the amount of killing when compared to either MGN or cefepime alone. The increase over cefepime killing is approximately one log.

The effect of the magainin/cefepime combination on the killing of *Pseudomonas aeruginosa* was also studied. As above, when magainin was present, there was a significant increase in the amount of killing when compared to that with either MGN or cefepime alone.

7. EXAMPLE: SYNERGISTIC ACTION OF CEPHALOSPORINS AND THE CATIONIC PEPTIDE C-13 OF HUMAN PLATELET FACTOR-4

In the example described herein, the synergistic action of the β-lactam antibiotic, a cephalosporin, and the C-13 human platelet factor-4 peptide (HPF-4) is demonstrated. In these experiments, sub-inhibitory concentrations of the cephalosporin and the C-13 human platelet factor-4 peptide when combined will kill bacteria. When either agent is administered alone, little or no killing results. These experiments were performed in 40% normal human serum. The synergy in serum requires a heat labile factor since mild heat inactivation of the serum totally abrogates any synergistic action.

7.1. MATERIALS AND METHODS

7.1.1. REAGENTS AND BUFFERS

The following buffers were used: gelatin-veronal buffer (GVB++) (Gewortz H. et al., 1985, in Manual of Clinical Immunology, N. R. Rose and H. Freedman (eds.) ASM, Washington, D.C.). In addition, 0.1% dextrose was added to the buffer as a carbon source. Phosphate buffered saline was prepared in house. Antibiotics were obtained in the lyophilized form as above. The C-13 PF-4 peptide was synthesized in house from the published amino acid sequence (Maione et al., 1990, Science 247:77–80). The modified C-13 PF-4 peptide was also synthesized in house by standard solid phase techniques.

7.1.2. BACTERIAL STRAINS AND CULTURE CONDITIONS

*Escherichia coli* ATCC 25922 was used for this experiment and was obtained from the American Type Culture Collection (ATCC). The strain was examined for purity, properly identified, and then stored at −70° C. It was grown in AMH.

7.1.3. SERUM

Blood was obtained from five healthy volunteers and was allowed to clot at room temperature for 1 hour. After an additional 20 min. incubation at 4° C. the blood was centrifuged for 15 min at 1,500×g. Serum was removed and pooled and was stored at −70° C. in small amounts (PNHS). Shortly before use, the sera was thawed and was kept on ice until mixed with bacteria for the serum bactericidal assay. Where indicated, serum complement was inactivated by heating at 56° C. for 30 min.

7.1.4. DETERMINATION OF THE MINIMUM INHIBITORY CONCENTRATION (MIC)

MIC's were determined by the microdilution plate dilution method using AMH (Manual of Clinical Microbiology, Fourth Edition, Lennette, E. H. Ed. in Chief, ASM. 1985. pps 972–977). At least three different determinations were performed with each antibiotic for each strain.

7.1.5. SERUM BACTERICIDAL ASSAY

Bacteria inoculated from overnight cultures were grown to mid log phase with or without antibiotic (absorbance at 660 nm between 0.35 and 0.5; approximately $2-3\times10^8$ cells/ml for cefepime grown and $9\times10^8$ cells/ml for grown without cefepime). Cells were diluted without washing to $1\times10^4$ cells/ml in gelatin-veronal buffer (GVB++) and 0.05 ml was added to serum in a 1.5 ml Eppendorf vial. Bacterial cells that were pregrown in antibiotic were also diluted in GVB++ containing the same concentration of antibiotic. Either PNHS or heat inactivated PNHS was prepared beforehand by dilution to the appropriate concentration in 0.2 ml of GVB++. Antibiotics or magainins when present, were added to the serum mixture before the addition of bacteria. The total reaction mixture was 0.25 ml. The number of bacteria added to serum was determined by adding 0.05 ml of the bacterial suspension to a tube containing only GVB++ and plating at the beginning of the assay. The reaction mixtures were then rotated at 37° C. up to three hours. Samples (25 μl) were removed at intervals for plate count analysis. The number of colony forming units was determined after overnight incubation of trypticase soy agar. Colony forming units were determined in triplicate and the average determined.

7.2. RESULTS

The bactericidal effect of the C-13 peptide obtained from human platelet factor 4 was studied. Based on the amino acid sequence of this cationic peptide, it should form an amphiphilic helix in hydrophobic environments. The ability of this peptide to kill *E. coli* was investigated in pooled normal human serum (FIG. 8). Bacterial cells grown with and without 1/5 MIC cefepime were added to active and heat inactivated 40% pooled normal human serum. As shown in FIG. 8, this peptide was able to significantly kill cefepime altered bacteria when sera had not been heat inactivated. The peptide was unable to kill bacteria that were not grown with cefepime. In addition, it did not kill cefepime altered bacteria when the serum was heat inactivated. This data clearly demonstrates that this peptide will kill bacteria synergistically with a β-lactam antibiotic and active serum.

The bactericidal effect of the modified C-13 peptide obtained from human platelet factor-4 having the sequence:

Pro-Leu-Tyr-Lys-Pro-Lys-Ile-Ile-Lys-Pro-Lys-Leu-Leu-Glu-Ser (Seq. I.D. #2) was also studied. When this sequence was added to bacteria along with cefepime in the presence of normal human sera, a lower or no synergistic effect was observed. This was due to a reduced α-helical character of the modified C-13 sequence since proline is known to disrupt α helices.

8. EXAMPLE: IN VIVO PROTECTIVE EFFECT OF MAGAININ AND CEFEPIME COMBINATIONS

The ability of magainin and cefepime combinations to protect mice from a lethal infection of *E. coli* was examined. Mice were made neutropenic by injection of Cytoxan and then challenged with *E. coli*. Mice were then divided into four different groups: (1) mice that were given no further treatment; (2) were given magainin 2 or C-13 peptide only; (3) were given cefepime only and (4) were given a combination of magainin 2 or C-13 peptide and cefepime. Mice were observed for 10 days following infection and the number of deaths recorded. The results of these studies clearly show that no treatment, treatment with magainin, C-13 peptide, or cefepime alone were insufficient to protect the mice from death. A combination of the magainin and cefepime or C-13 peptide and cefepime resulted in significant protection of the mice. When amikacin, an aminoglycoside, was tested in similar experiments, no in vitro bactericidal activity or in vivo protection was found.

8.1. MATERIALS AND METHODS

8.1.1. REAGENTS AND BUFFERS

Phosphate buffered saline was prepared in house. Cefepime was obtained in the lyophilized form as above. C-13 peptide and Magainin 2 were synthesized in house from the published amino acid sequence.

8.1.2. BACTERIAL STRAINS AND CULTURE CONDITIONS

*E. coli* H16 was obtained from Walter Reed Army Institute of Research, Department of Bacterial Diseases, Washington, D.C. The strain was examined for purity, properly identified, and then stored at −70° C. The bacteria was grown in AMH broth.

8.1.3. IN VIVO EXPERIMENTS

Mice were made neutropenic five days prior to bacterial challenge. Neutropenia was induced by subcutaneous injection of 250 mg/kg Cytoxan (cyclophosphamide). The mice were challenged with $2\times10^4$ *E. coli* H16. Challenge was by intraperitoneal injection. Mice was then divided into four groups: (1) mice were given injections of PBS at 1 and 3.5 hrs after the bacterial challenge were administered; (2) mice were given a total of 2 mg/mouse magainin 2 by two injections at 1 and 3.5 hr after bacterial challenges of 1 mg/mouse in PBS; (3) mice were given a total of 0.2 mg/kg cefepime by two injections at 1 and 3.5 hr after bacterial challenge of 0.1 mg/kg cefepime in PBS; (4) mice were given a total of 2 mg/mouse magainin 2 and 0.2 mg/kg cefepime by two injections at 1 and 3.5 hr after bacterial challenge of 1 mg/mouse magainin 2 and 0.1 mg/kg cefepime. All injections of magainin and cefepime were administered intramuscularly. The survival of the mice was monitored for a period of at least 10 days

8.2. RESULTS

When mice were examined for survival after bacterial challenge the following results were obtained: in group 1, where only PBS was administered, 1 out of 15 mice survived; in group 2 where only magainin 2 was administered, 1 out of 15 mice survived; in group 3 where cefepime alone was administered, 1 out of 20 mice survived; and in group 4 where the combination of magainin 2 and cefepime was administered 11 out of 20 mice survived. The increase in the survival of mice which were given the combination represents a significant (p<0.05, Fisher Exact test) increase in protection from either no treatment or treatment with either cefepime or magainin 2 alone.

In addition, similar animal protection experiments were performed with peptide C-13 from PF-4. In these experiments, in addition to groups 1 and 3 above; group 2 was modified to contain C-13 peptide instead of magainin 2 and group 4 was modified to contain the combination of C-13 and cefepime. The results of this experiment were as follows: Groups 1 and 3 were as described above; in Group 2 where C-13 was administered alone 1 out of 10 mice survived; in Group 4 where the combination of the C-13 peptide and cefepime was administered, 4 out of 10 mice survived. This represents an improvement in survival for those mice given the combination of the C-13 peptide and cefepime.

Combinations of amikacin, an aminoglycoside, and magainin 2 were also examined in vivo. After determining the MIC for amikacin and dividing the mice into four groups similar to those above, the following results were obtained: PBS alone zero out of eight mice survived; magainin 2 (two injections 1 mg/mouse) zero out of nine mice survived; amikacin (two injections of 3 mg/kg) three out of 10 mice survived and magainin 2 and amikacin (at the dosages above) one out of 10 mice survived.

9. EXAMPLE: SYNTHESIS OF ANALOGS OF C-13 PEPTIDE

Various analogs of the C-13 peptide (Table 1) have been made by solid phase techniques. The analogs were designed so as to alter the physical parameters of the C-13 peptide in specific ways. Certain of the alterations in physical parameters affected the interaction of the peptide analog with the bacterial membrane. Lengthening the molecule to add an additional α helical turn, and changing the positive charge density along the helices were found to invoke changes in synergistic activity with cefepime.

9.1 MATERIALS AND METHODS

9.1.1. REAGENTS AND METHODS

Magainin 2, cecropin and analogs of C-13 peptide were synthesized by solid phase synthetic techniques (Merrifield, R. B. 1963. J. Am. Chem. Soc. 85:2149–2154) on an Applied Biosystems Peptide Synthesizer Model 430A using Boc/benzyl based protection. The assembled peptide resin was treated by the low/high HF procedure (Tam, J. P. et al., 1983. J. Am. Chem. Soc. 105:6402–6455) or by the standard high HF procedure with 90% HF/10% anisole and then cleaved. Deprotected peptide was purified by high performance liquid chromatography (HPLC) on a Dynamax C-8 column (Rainin). Purified peptides were characterized by standard analytical HPLC and amino acid analysis methods.

TABLE 1

ANALOGS OF C-13 PEPTIDE

| NUMBER | SEQUENCE I.D. NUMBER | Amino Acid Sequence |
|---|---|---|
| C-13 | 1 | Pro—Leu—Tyr—Lys—Lys—Ile—Ile—Lys—Lys—Leu—Leu—Glu—Ser |
| B | 3 | Pro—Leu—Lys—Lys—Tyr—Ile—Ile—Lys—Lys—Glu—Leu—Leu—Ser |
| W | 4 | Pro—Leu—Tyr—Lys—Lys—Pro—Ile—Lys—Lys—Pro—Leu—Glu—Ser |
| H | 5 | Ala—Leu—Tyr—Lys—Lys—Ile—Ile—Lys—Lys—Leu—Leu—Glu—Ser—Ala—Lys—Lys—Leu—Gly |
| F | 6 | Ala—Leu—Tyr—Lys—Lys—Leu—Leu—Lys—Lys—Leu—Leu—Glu—Ser—Ala—Lys—Lys—Leu—Gly |
| G | 7 | Ala—Leu—Tyr—Lys—Lys—Leu—Leu—Lys—Lys—Leu—Leu—Lys—Ser—Ala—Lys—Lys—Leu—Gly |
| X |  | dAla—dLeu—dTyr—dLys—dLys—dLeu—dLeu—dLys—dLys—dLeu—dLeu—dLys—dSer—dAla—dLys—dLys—dLeu—Gly |
| II |  | Ala—Leu—Tyr—Orn—Orn—Leu—Leu—Orn—Orn—Leu—Leu—Orn—Ser—Ala—Orn—Orn—Leu—Gly |
| KK | 8 | Ala—Leu—Tyr—Lys—Lys—Leu—Leu—Lys—Lys—Leu—Leu—Lys—Lys—Ala—Lys—Lys—Leu—Gly |
| HH | 9 | Ala—Leu—Tyr—Arg—Arg—Leu—Leu—Arg—Arg—Leu—Leu—Arg—Ser—Ala—Arg—Arg—Leu—Gly |
| P | 10 | Ala—Leu—Tyr—Lys—Lys—Leu—Leu—Lys—Lys—Leu—Leu—Lys—Phe—Ala—Lys—Lys—Phe—Gly |
| N | 11 | Lys—Trp—Lys—Leu—Tyr—Lys—Lys—Leu—Leu—Lys—Lys—Leu—Leu—Lys—Ser—Ala—Lys—Lys—Leu—Gly |
| J | 12 | Ala—Lys—Lys—Leu—Ala—Lys—Leu—Tyr—Lys—Lys—Leu—Leu—Lys—Lys—Leu—Leu—Lys—Ser—Ala—Lys—Lys—Leu—Gly |

10. EXAMPLE: IN VIRTO SCREENING OF C-13 PEPTIDE ANALOGS FOR BACTERICIDAL ACTIVITY AND HEMOLYTIC ACTIVITY

Synthetically produced analogs of the C-13 peptide of platelet factor-4 were tested for synergistic activity with cefepime in in vitro bactericidal and hemolytic assays. Peptides which were at least about 11 to 18 amino acids in length, forming about 4 or 5 α helical turns reduced the amount of peptide required to kill one half of the bacterial cells by a factor of 8 to 80.

Peptide analogs which disrupted the α helical nature of the peptide or its amphiphilicity reduced or obviated any bactericidal activity. The addition of amino acids to form a fifth α helical loop improved bactericidal activity. This activity was further improved by altering the positive charge density along the helix.

C-13 peptide analogs H, F, and to a lesser extent G, X and L were found to give improved bactericidal cell killing when used in combination with antibiotic. Analogs H, F, G, X, II, KK, N and J were found to require complement or gave greatly improved bactericidal results when complement was present in the screening medium. Increases in the hemolytic activity of the C-13 peptide analogs were encountered when the peptide was increased in length in the amino direction or when arginine replaced lysine at positions 4, 5, 8, 9, 12, 15, and 16.

10.1. MATERIALS AND METHODS

10.1.1. REAGENTS AND BUFFERS

The following buffers were used: gelatin-veronal buffer (GVB++ as described above). In addition, 0.1% dextrose was added to the buffer as a carbon source. Phosphate buffered saline was prepared in house. Antibiotics, i.e., cefepime, were obtained in the lyophilized form as described above.

10.1.2. BACTERIAL STRAINS AND CULTURE CONDITIONS

*Escherichia coli* strain ATCC 25922 was used for most of the experiments and was obtained from the American Type Culture Collection. Other *E. coli* strains used were A011 obtained from Harborview Medical Center, Seattle, Wash., a K1 capsule isolate H16 from Walter Reed Army Institute of Research, Washington, D.C. *E. coli* A645AP, generated in house, is an animal-passed version of ATCC 25922, *E. coli* A645AP (pBR322) is *E. coli* A645AP containing plasmid pBR322 to confer resistance to $\beta$-lactam antibiotics and was generated in house. *Klebsiella pneumoniae* C329 (ATCC 13883) was obtained from the American Type Culture Collection as was *Pseudomonas aeruginosa* strain A366 (ATCC 27317). *Staphylococcus aureus* strain A546 was obtained from Harborview Medical Center, Seattle, Wash. *Enterobacter aerogenis* strain G438 was obtained from the Veterans Administration Hospital, Seattle, Wash. and *Streptococcus agarlactiae* strain I334 was obtained from Childrens Orthopedic Hospital, Seattle, Wash. The antibiotic resistant *Pseudomonas aeruginosa* strain M990 was obtained from the in house culture collection. Strains were examined for purity, properly identified, and then stored at $-70°$ C. Each week new cultures were made from the frozen bacterial stocks to avoid repetitive subculturing. All strains were grown in Adjusted Mueller Hinton broth (AMH) containing 50 $\mu g/1$ $CaCl_2$ and 25 mg/l $MgCl_2$.

10.1.3. SERUM BACTERICIDAL ASSAY

Bacteria, all strains, inoculated from overnight cultures were grown to mid log phase with or without $\frac{1}{4}$ or 1/5 MIC cefepime (Absorbance at 660 nm between 0.35 and 0.5; approximately $2-3 \times 10^8$ cells/ml for cell grown with cefepime and $9 \times 10^8$ cells/ml cells grown without cefepime). Cells were diluted without washing to $5 \times 10^4$ cells/ml gelatin-veronel buffer (GBV++) and 0.05 ml was added to serum (see section 7.1.3.) in a 1.5 ml Eppendorf vial. For those bacterial cells pregrown in cefepime, the same amount of cefepime that was present during growth was added for both the preparation and examination of bactericidal activity. Either pooled normal human serum or heat inactivated serum was prepared beforehand by dilution to the appropriate concentration in 0.2 ml of GVB++. Cefepime, when present, was added to the serum mixture before the addition of bacterial cells. Peptides were diluted in deionized water to make a stock solution of 2 mg/ml and added to the reaction vial to give the appropriate concentration. The total reaction volume was 0.25 ml. The number of bacteria added to the serum was determined by adding 0.05 ml of the bacterial suspension to a tube containing only GVB++ and plating at the beginning of the assay. The reaction mixtures were then rotated at 37° C. for three hours. Samples (25 $\mu$l) were removed at intervals for plate count analysis. The number of colony forming units was determined after overnight incubation with trypticase soy agar. Colony forming units were determined in triplicate and the average determined.

10.1.4. HEMOLYSIS ASSAY

Whole blood obtained from healthy volunteers was diluted in PBS to give a concentration of red blood cells of approximately $6 \times 10^8$ cells/ml. Peptides were suspended in PBS to make stock solution of 2 mg/ml and 100 $\mu$l stock solution was added to 900 $\mu$l of the diluted red blood cells. Samples were incubated at 37° C. for 45 minutes, centrifuged at $1000 \times g$ for 5 minutes and the supernatant removed. Supernatants were examined spectrophotometrically at 541 nm. Percent hemolysis was read from a standard curve, prepared from a dilution series of blood diluted 1:10 in distilled water. A dilution of 1:10 in distilled water represented 100% hemolysis.

TABLE 2

IN VITRO BACTERICIDAL $(ID_{50})[1]$ AND HEMOLYTIC ACTIVITY OF CATIONIC OLIGOPEPTIDES WITH *E. COLI* A645 (ATCC 25922)

| PEP-TIDE | NO CEFEPIME | | $\frac{1}{4}$ MIC CEFEPIME[1] | | RBC LYSIS (%) (100 $\mu$G/ML) |
|---|---|---|---|---|---|
| | NHS | HI-NHS | NHS | HI-NHS | |
| MGN 2 | >200 | >200 | 85 | >200 | 1 |
| C-13 | >200 | >200 | 80 | >200 | <1 |
| B | >200 | >200 | >200 | >200 | ND[3] |
| W[1] | >200 | >200 | >200 | >200 | ND |
| H | >100 | >100 | 10 | >100 | 1.5 |
| F | 70 | >200 | 10 | 90 | <1 |
| G | 4 | >200 | 1 | >200 | <1 |
| X | 4 | >50 | <1 | >50 | <1 |
| HH[2] | >50 | >50 | >50 | >50 | 3 |
| II[2] | 1 | 47 | <1 | 43 | <1 |
| KK | 1 | >50 | <1 | >50 | <1 |
| P | 10 | 10 | 10 | 10 | 21 |
| L | 46 | 40 | 11 | 40 | 3 |
| N | 1 | 10 | 1 | >2 | 7.5 |
| J | 1 | >8 | 1 | 4 | 2.5 |
| Cecropin | 1 | 1 | .25 | .5 | <1 |

[1]$ID_{50}$ — Represents the amount of peptide ($\mu$g/ml) required to reduce the bacterial input by 50%.
[2]1/5 MIC cefepime
[3]ND — Not Determined

10.2 RESULTS

The bactericidal effect of various cationic oligopeptides with and without antibiotic and with and without active complement have been tested including magainins, cecropin, the C-13 peptide of IIPF-4 and various analogs and derivatives of the C-13 peptide (Table 2). Additionally the potential for toxicity was monitored by examining the ability of the peptides to lyse human red blood cells. Initially two different aspects of secondary structure were examined. Peptides containing amino acid substitutions that disrupted either the amphipathic (analog B) or the alpha helical nature (analog W) of the molecule were inactive in all test conditions. Since both the alpha helical and amphipathic nature of the peptide were required for activity all subsequent modifications maintained both of these parameters. A modification that incorporated another turn in the alpha helix by the addition of five amino acids and maintained the amphipathic nature was examined (analog H). This modification specifically potentiated killing with cefepime in NHS. There was an eight fold increase in the antimicrobial activity (peptide analog H) against cefepime altered bacteria in NHS, however a corresponding increase was not observed in HI-NHS or against untreated bacteria. A minor change in analog H of two hydrophobic amino acids (analog F) resulted in a slight increase in antimicrobial activity. A ten fold increase in activity specific for cefepime altered bacteria in NHS was observed when a glutamic acid residue in analog F was replaced with lysine (analog G). No corresponding increase in antimicrobial activity was observed with this peptide in HI-NHS or when examined against untreated bacteria. In addition no increase in the amount of red blood cell (RBC) lysis was observed. Peptide analog G demonstrated that a change in a single charge could greatly influence activity.

Extending the helix with another turn by the addition of an five amino acids on the amino terminus (analog J) resulted in no additional increase in antibacterial activity. This modification increased the amount of RBC lysis. This may indicate that peptides with a greater number of helical turns are toxic. The in vitro analysis of antimicrobial activity in NHS with cefepime resulted in a peptide (analog G) with an 80 fold increase in antibacterial activity. In stark contrast there was no antimicrobial activity in HI-NHS or against untreated bacteria. Further examination of analog G revealed that bactericidal activity is dependent upon NHS with other bacterial strains (Table 3). This data also indicates that the bactericidal activity of analog G with normal human sera can be enhanced by antibiotic to a varying degree depending upon the bacterial strain.

TABLE 3

IN VITRO BACTERICIDAL ACTIVITY $(ID_{50})^1$ OF C-13 PEPTIDE ANALOG G AGAINST DIFFERENT BACTERIAL STRAINS

| STRAIN | NO CEFEPIME | | ¼ MIC CEFEPIME[2] | | % SERA | MIC |
|---|---|---|---|---|---|---|
| | NHS | HI-NHS | NHS | HI-NHS | | |
| H16 | >200 | >200 | 15 | 100 | 40 | ⅛ |
| C329 | 1 | 80 | 1 | 50 | 10 | ⅛ |
| G438 | 1 | 45 | 1 | 45 | 10 | ⅛ |
| A366 | <25 | 40 | <25 | 40 | 10 | ⅛ |
| A011 | 2 | 80 | 2 | 80 | 10 | ⅛ |
| A586 | >200 | >200 | >200 | >200 | 40 | SL[3] |
| 1334 | >200 | 45 | 80 | 25 | 40 | ⅛ |
| A645AP | 1 | 70 | 1 | 80 | 10 | ⅛ |
| A645AP[2] (pBR322) | 1 | 70 | ND | 80 | 10 | ⅛ |
| M009[2] | 2 | 120 | ND | ND | 20 | ⅛ |

[1]$ID_{50}$ — Represents the amount of peptide & μg/ml) required to reduce the bacterial input by 50%
[2]Antibiotic resistant strains MIC A645AP (pBR322), 1 ug/ml; MIC M009, 64 ug/Ml
[3]A sublethal (SL) concentration of cefepime was determined by dilution of the antibiotic in broth and examination of growth after three hours.

11. EXAMPLE: IN VIVO PROTECTIVE EFFECT OF C-13 PEPTIDE ANALOGS AND CEFEPIME COMBINATIONS

The ability of C-13 peptide analogs and cefepime combinations to protect mice from a lethal infection of *E. coil* was examined. Mice were made neutropenic by an injection of cyclophosphamide and then challenged with *E. coli*. Mice were then divided into four groups: (1) mice that were given PBS; (2) were given C-13 peptide analogs only; (3) were given cefepime only; and (4) were given a combination of C-13 peptide analogs and cefepime. Mice were observed for 10 days following infection and the numbers of deaths recorded. The results of these studies clearly show that no treatment, treatment with cefepime alone, or with C-13 peptide analogs G, X, II and F were insufficient to protect the mice from death. A combination of the C-13 peptide analogs and cefepime resulted in significant protection of the mice.

11.1. MATERIALS AND METHODS

11.1.1. REAGENTS AND BUFFERS

Phosphate buffered saline was prepared in house cefepime was obtained from Dr. Robert Kessler, Bristol-Myers Squibb Company, Wallingford, Conn. in the lyophilized form. Cecropin was synthesized in house from the published sequence. Cyclophosphamide was purchased from Mead Johnson under the Tradename Cytoxan.

11.1.2 BACTERIAL STRAINS AND CULTURE CONDITIONS

*E. coli* H16 was obtained from Walter Reed Army Institute of Research, Washington, D.C. and *E. coli* A645AP was generated by animal passage of *E. coli* ATCC 25922 in house. The strains were examined for purity, properly identified, and then stored at −70° C. Each week new cultures were made from the frozen bacterial stocks to avoid repetitive subculturing. All strains were grown in Adjusted Mueller Hinton broth containing 50 mg/l $CaCl_2$ and 25 mg/l $MgCl_2$.

11.1.3. IN VIVO EXPERIMENTS

Male CrL:CF1 mice were made neutropenic five days prior to bacterial challenge. Neutropenia was induced by subcutaneous injection of 250 mg/kg Cytoxan (cyclophosphamide). The mice were challenged with either $2 \times 10^4$ *E. coli* H16 (Table 4) or $5 \times 10^4$ A645AP by intraperitoneal injection. Mice were divided into four treatment groups: (1) PBS; (2) C-13 peptide analog (15 mg/kg); (3) cefepime (0.1 mg/kg); (4) a combination treatment of cefepime and C-13 peptide analog (0.1 mg/kg cefepime and 15 mg/kg C-13 peptide analog) that were combined prior to injection. All injections were made in PBS (0.2 ml) and were administered intramuscularly with each injection in separate legs, one and 3.5 hours after bacterial challenge. The survival of the mice was monitored for ten days and the results analyzed by the Fisher Exact test.

11.2. RESULTS

The effect of C-[3 peptide analogs and cefepime to protect mice from a systemic *E. coli* H16 infection was examined (Table 4). PBS, cefepime or C-13 peptide analogs G, X, II, and F when administered alone failed to provide a significant level of protection. In contrast a significant ($p < 0.05$, Fisher Exact test) increase in survival of mice which were given the combination of cefepime and C-13 peptide analog G, or F was observed when compared to either no treatment or treatment with either cefepime or C-13 peptide analog alone. In addition similar experiments were carried out with cecropin which resulted in no significant increase in protection when used alone or in combination with cefepime.

Further, aztreonam, another antibiotic, was tested in similar experiments. This β-lactam antibiotic, when combined with C-13 peptide analog G yielded statistically significant protection ($p < 0.05$, Fisher Exact test). The results of the experiments are as follows: when PBS administered alone, zero out of nine mice survived;

where aztreonam alone was administered one out of 20 mice survived; where C-13 peptide analog G was administered alone zero out of 10 mice survived; where aztreonam and C-13 analog G were administered 11 out of 20 mice survived.

C-13 peptide analog G was also examined in neutropenic mice challenged with the non K1 *E. coli* strain A645AP ($5.0 \times 10^4$ organisms). When mice were examined for survival after bacterial challenge the following results were obtained: in group 1, where only PBS was administered 3 out of 20 mice survived; in group 2, where only G was administered, 0 out of 15 survived; in group 3 where cefepime was administered 3 out of 20 survived; and in group 4, where both G and cefepime were administered 8 out of 15 survived. The increase in survival of mice which were given the combination was again significant ($p < 0.05$, Fisher Exact test) and represents an improvement in survival over peptide or antibiotic given alone.

TABLE 4

EFFECT OF C-13 PEPTIDE ANALOGS AND CEFEPIME ON SYSTEMIC E. COLI INFECTION

| Treatment | Number—Survived/Total | % Survival |
|---|---|---|
| PBS | 2/25 | 8 |
| cefepime | 3/25 | 12 |
| G | 1/15 | 6.7 |
| cefepime + G | 11/20 | 55 |
| X | 1/18 | 5.6 |
| cefepime + X | 15/20 | 75 |
| II | 0/5 | |
| cefepime + II | 3/10 | 30 |
| F | 0/10 | |
| cefepime + F | 3/10 | 30 |
| Cecropin | 2/20 | 20 |
| cefepime + Cecropin | 2/10 | 20 |

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

We claim:

1. A composition for treating an infection caused by an organism susceptible to a β-lactam antibiotic comprising:
  (a) a β-lactam antibiotic capable of inhibiting the growth of the organism; and
  (b) a cationic oligopeptide having an amino acid residue sequence:
    $aa_1$-Leu-Tyr-Lys-$aa_2$-$aa_2$-Lys-Lys-Leu-Leu-$aa_3$-$aa_4$-X;
  wherein $aa_1$ is Pro, Ala or Lys, $aa_2$ is Ile or Leu, $aa_3$ is Glu or Lys, $aa_4$ is Ser, Leu or Lys and X is a carboxyl group or a five amino acid residue sequence being alpha helical in nature, and having the general sequence of $aa_5$-Lys-Lys-$aa_6$-Gly, wherein $aa_5$ is Ala or Leu and $aa_6$ is Leu or Phe.

2. A composition for treating an infection caused by Enterobacteriaceae bacteria comprising:
  (a) a β-lactam antibiotic capable of inhibiting the growth of the Enterobacteriaceae bacteria; and
  (b) a cationic oligopeptide having an amino acid residue sequence:
    $aa_1$-Leu-Tyr-Lys-$aa_2$-$aa_2$-Lys-Lys-Leu-Leu-$aa_3$-$aa_4$-X;
  wherein $aa_1$ is Pro, Ala or Lys, $aa_2$ is Ile or Leu, $aa_3$ is Glu or Lys, $aa_4$ is Ser, Leu or Lys and X is a carboxyl group or a five amino acid residue sequence being alpha helical in nature, and having the general sequence of $aa_5$-Lys-Lys-$aa_6$-Gly, wherein $aa_5$ is Ala or Leu and $aa_6$ is Leu or Phe.

3. A composition for treating a bacterial infection caused by *Escherichia coli* comprising:
  (a) cefepine; and
  (b) a cationic oligopeptide having an amino acid residue sequence:
    $aa_1$-Leu-Tyr-Lys-$aa_2$-$aa_2$-Lys-Lys-Leu-Leu-$aa_3$-$aa_4$X;
  wherein $aa_1$ is Pro, Ala or Lys, $aa_2$ is Ile or Leu, $aa_3$ is Glu or Lys, $aa_4$ is Ser, Leu or Lys and X is a carboxyl group or a five amino acid residue sequence being alpha helical in nature, and having the general sequence of $aa_5$-Lys-Lys-$aa_6$-Gly, wherein $aa_5$ is Ala or Leu and $aa_6$ is Leu or Phe.

4. A method for treating an infection caused by an organism susceptible to a β-lactam antibiotic comprising administering to a patient a therapeutically effective amount of a composition comprising:
  (a) a β-lactam antibiotic capable of inhibiting the growth of the organism, and
  (b) a cationic oligopeptide having an amino acid residue sequence:
    $aa_1$-Leu-Tyr-Lys-$aa_2$-$aa_2$-Lys-Lys-Leu-Leu-$aa_3$-$aa_4$-X;
  wherein $aa_1$ is Pro, Ala or Lys, $aa_2$ is Ile or Leu, $aa_3$ is Glu or Lys, $aa_4$ is Ser, Leu or Lys and X is a carboxyl group or a five amino acid residue sequence being alpha helical in nature, and having the general sequence of $aa_5$-Lys-Lys-$aa_6$-Gly, wherein $aa_5$ is Ala or Leu and $aa_6$ is Leu or Phe for a time sufficient to inhibit the growth of the organism.

5. A method for treating an Enterobacteriaceae bacterial infection comprising administering to a patient a therapeutically effective amount of a composition comprising:
  (a) a β-lactam antibiotic capable of inhibiting the growth of the Enterobacteriaceae bacteria; and
  (b) a cationic oligopeptide corresponding to an amino acid residue sequence comprising:
    $aa_1$-Leu-Tyr-Lys-$aa_2$-$aa_2$-Lys-Lys-Leu-Leu-$aa_3$-$aa_4$-X;
  wherein $aa_1$ is Pro, Ala or Lys, $aa_2$ is Ile or Leu, $aa_3$ is Glu or Lys, $aa_4$ is Ser, Leu or Lys and X is a carboxyl group or a five amino acid residue sequence being alpha helical in nature, and having the general sequence of $aa_5$-Lys-Lys-$aa_6$-Gly, wherein $aa_5$ is Ala or Leu and $aa_6$ is Leu or Phe for a time period sufficient to inhibit the growth of the organism.

6. The composition of claim 1, wherein the β-lactam antibiotic is selected from the group consisting of a penicillin, a cephalosporin, a carbapenem, a monobactam, a cephamycin, a pyrazidon and a penem.

7. The composition of claim 2, wherein the β-lactam antibiotic is a cephalosporin.

8. The composition of claim 7, wherein the cephalosporin is selected from the group consisting of cefepime, cefotaxime and ceftazidime.

9. The composition of claim 6, wherein the β-lactam antibiotic is a carbapenem.

10. The composition of claim 9, wherein the carbapenem is imipenem.

11. The composition of claim 6, wherein the β-lactam antibiotic is a monobactam.

12. The composition of claim 11, wherein the monobactam is aztreonam.

13. The composition of claim 1, wherein the cationic oligopeptide comprises an amino acid residue sequence selected from the group consisting of:
  Pro-Leu-Tyr-Lys-Lys-Ile-Ile-Lys-Lys-Leu-Leu-Glu-Ser (Seq ID #1);
  Ala-Leu-Tyr-Lys-Lys-Ile-Ile-Lys-Lys-Leu-Leu-Glu-Ser-Ala-Lys-Lys-Leu-Gly (Seq. ID #5);
  Ala-Leu-Tyr-Lys-Lys-Leu-Leu-Lys-Lys-Leu-Leu-Glu-Ser-Ala-Lys-Lys-Leu-Gly (Seq. ID #6);
  Ala-Leu-Tyr-Lys-Lys-Leu-Leu-Lys-Lys-Leu-Leu-Lys-Ser-Ala-Lys-Lys-Leu-Gly (Seq. ID #7);

Ala-Leu-Tyr-Lys-Lys-Leu-Leu-Lys-Lys-Leu-Leu-
 Lys-Lys-Ala-Lys-Lys-Leu-Gly (Seq. ID #8);
Ala-Leu-Tyr-Lys-Lys-Leu-Leu-Lys-Lys-Leu-Leu-
 Lys-Phe-Ala-Lys-Lys-Phe-Gly (Seq. ID #10);
Lys-Trp-Lys-Leu-Tyr-Lys-Lys-Leu-Leu-Lys-Lys-
 Leu-Leu-Lys-Ser-Ala-Lys-Lys-Leu-Gly (Seq. ID #11); and
Ala-Lys-Lys-Leu-Ala-Lys-Leu-Tyr-Lys-Lys-Leu-
 Leu-Lys-Lys-Leu-Leu-Lys-Ser-Ala-Lys-Lys-Leu-
 Gly (Seq. ID #12).

14. The composition of claim 1 wherein the cationic oligopeptide comprises the amino acid residue sequence:
Ala-Leu-Tyr-Lys-Lys-Leu-Leu-Lys-Lys-Leu-Leu-
 Lys-Ser-Ala-Lys-Lys-Leu-Gly;
wherein the amino acid residues can be d-amino acids.

15. The composition of claim 1, wherein the cationic oligopeptide comprises the amino acid sequence:
Ala-Leu-Tyr-Orn-Orn-Leu-Leu-Orn-Orn-Leu-Leu-
 Orn-Ser-Ala-Orn-Orn-Leu-Gly.

16. The composition of claim 2, wherein the β-lactam antibiotic is selected from the group consisting of a penicillin, a cephalosporin, a carbapenem, a monobactam, a cephamycin, a pyrazidon and a penem.

17. The composition of claim 16, wherein the β-lactam antibiotic is a cephalosporin.

18. The composition of claim 17, wherein the cephalosporin is selected from the group consisting of cefepime, cefotaxime and ceftazidime.

19. The composition of claim 16, wherein the β-lactam antibiotic is a carbapenem.

20. The composition of claim 19, wherein the carbapenem is imipenem.

21. The composition of claim 16, wherein the β-lactam antibiotic is a monbactam.

22. The composition of claim 21, wherein the monobactam is aztreonam.

23. The composition of claim 2, wherein the cationic oligopeptide comprises an amino acid residue sequence selected from the group consisting of:
Pro-Leu-Tyr-Lys-Lys-Ile-Ile-Lys-Lys-Leu-Leu-Glu-
 Ser (Seq ID #1);
Ala-Leu-Tyr-Lys-Lys-Ile-Ile-Lys-Lys-Leu-Leu-Glu-
 Ser-Ala-Lys-Lys-Leu-Gly (Seq. ID #5);
Ala-Leu-Tyr-Lys-Lys-Leu-Leu-Lys-Lys-Leu-Leu-
 Glu-Ser-Ala-Lys-Lys-Leu-Gly (Seq. ID #6);
Ala-Leu-Tyr-Lys-Lys-Leu-Leu-Lys-Lys-Leu-Leu-
 Lys-Ser-Ala-Lys-Lys-Leu-Gly (Seq. ID #7);
Ala-Leu-Tyr-Lys-Lys-Leu-Leu-Lys-Lys-Leu-Leu-
 Lys-Lys-Ala-Lys-Lys-Leu-Gly (Seq. ID #8);
Ala-Leu-Tyr-Lys-Lys-Leu-Leu-Lys-Lys-Leu-Leu-
 Lys-Phe-Ala-Lys-Lys-Phe-Gly (Seq. ID #10);
Lys-Trp-Lys-Leu-Tyr-Lys-Lys-Leu-Leu-Lys-Lys-
 Leu-Leu-Lys-Ser-Ala-Lys-Lys-Leu-Gly (Seq. ID #11); and
Ala-Lys-Lys-Leu-Ala-Lys-Leu-Tyr-Lys-Lys-Leu-
 Leu-Lys-Lys-Leu-Leu-Lys-Ser-Ala-Lys-Lys-Leu-
 Gly (Seq. ID #12).

24. The composition of claim 2, wherein the cationic oligopeptide comprises the amino acid residue sequence:
Ala-Leu-Tyr-Lys-Lys-Leu-Leu-Lys-Lys-Leu-Leu-
 Lys-Ser-Ala-Lys-Lys-Leu-Gly;
wherein the amino acid residues can be d-amino acids.

25. The composition of claim 2, wherein the cationic oligopeptide comprises the amino acid residue sequence:
Ala-Leu-Tyr-Orn-Orn-Leu-Leu-Orn-Orn-Leu-Leu-
 Orn-Ser-Ala-Orn-Orn-Leu-Gly.

26. A composition for treating an infection caused by *Escherichia coli* comprising:
(a) cefepime and (b) a C-13 peptide of human platelet factor-4 comprising the amino acid residue sequence:
Pro-Leu-Tyr-Lys-Lys-Ile-Ile-Lys-Lys-Leu-Leu-
 Glu-Ser (Seq. I.D. #1).

27. The composition of claim 3, wherein the cationic oligopeptide comprises an amino acid residue sequence selected from the group consisting of:
Pro-Leu-Tyr-Lys-Lys-Ile-Ile-Lys-Lys-Leu-Leu-Glu-
 Ser (Seq ID #1);
Ala-Leu-Tyr-Lys-Lys-Ile-Ile-Lys-Lys-Leu-Leu-Glu-
 Ser-Ala-Lys-Lys-Leu-Gly (Seq. ID #5);
Ala-Leu-Tyr-Lys-Lys-Leu-Leu-Lys-Lys-Leu-Leu-
 Glu-Ser-Ala-Lys-Lys-Leu-Gly (Seq. ID #6);
Ala-Leu-Tyr-Lys-Lys-Leu-Leu-Lys-Lys-Leu-Leu-
 Lys-Ser-Ala-Lys-Lys-Leu-Gly (Seq. ID #7);
Ala-Leu-Tyr-Lys-Lys-Leu-Leu-Lys-Lys-Leu-Leu-
 Lys-Lys-Ala-Lys-Lys-Leu-Gly (Seq. ID #8);
Ala-Leu-Tyr-Lys-Lys-Leu-Leu-Lys-Lys-Leu-Leu-
 Lys-Phe-Ala-Lys-Lys-Phe-Gly (Seq. ID #10);
Lys-Trp-Lys-Leu-Tyr-Lys-Lys-Leu-Leu-Lys-Lys-
 Leu-Leu-Lys-Ser-Ala-Lys-Lys-Leu-Gly (Seq. ID #11); and
Ala-Lys-Lys-Leu-Ala-Lys-Leu-Tyr-Lys-Lys-Leu-
 Leu-Lys-Lys-Leu-Leu-Lys-Ser-Ala-Lys-Lys-Leu-
 Gly (Seq. ID #12).

28. The composition of claim 27, wherein the cationic oligopeptide comprises the amino acid residue sequence:
Ala-Leu-Tyr-Lys-Lys-Leu-Leu-Lys-Lys-Leu-Leu-
 Lys-Ser-Ala-Lys-Lys-Leu-Gly
wherein the amino acid residues can be d-amino acids.

29. The composition of claim 3, wherein the cationic oligopeptide comprises the amino acid residue following sequence:
Ala-Leu-Tyr-Orn-Orn-teu-Leu-Orn-Orn-Leu-Leu-
 Orn-Ser-Ala-Orn-Orn-Leu-Gly.

30. The method of claim 3, wherein the amount of the β-lactam antibiotic is a sub-inhibitory dosage.

31. The method of claim 4, wherein the β-lactam antibiotic is selected from the group consisting of a penicillin, a cephalosporin, a carbapenem, a monobactam, a cephamycin, a pyrazidon and a penem.

32. The method of claim 4, wherein the cationic oligopeptide comprises an amino acid residue sequence selected from the group consisting of:
Pro-Leu-Tyr-Lys-Lys-Ile-Ile-Lys-Lys-Leu-Leu-Glu-
 Ser (Seq ID #1);
Ala-Leu-Tyr-Lys-Lys-Ile-Ile-Lys-Lys-Leu-Leu-Glu-
 Ser-Ala-Lys-Lys-Leu-Gly (Seq. ID #5);
Ala-Leu-Tyr-Lys-Lys-Leu-Leu-Lys-Lys-Leu-Leu-
 Glu-Ser-Ala-Lys-Lys-Leu-Gly (Seq. ID #6);
Ala-Leu-Tyr-Lys-Lys-Leu-Leu-Lys-Lys-Leu-Leu-
 Lys-Ser-Ala-Lys-Lys-Leu-Gly (Seq. ID #7);
Ala-Leu-Tyr-Lys-Lys-Leu-Leu-Lys-Lys-Leu-Leu-
 Lys-Lys-Ala-Lys-Lys-Leu-Gly (Seq. ID #8);
Ala-Leu-Tyr-Lys-Lys-Leu-Leu-Lys-Lys-Leu-Leu-
 Lys-Phe-Ala-Lys-Lys-Phe-Gly (Seq. ID #10);
Lys-Trp-Lys-Leu-Tyr-Lys-Lys-Leu-Leu-Lys-Lys-
 Leu-Leu-Lys-Ser-Ala-Lys-Lys-Leu-Gly (Seq. ID #11); and
Ala-Lys-Lys-Leu-Ala-Lys-Leu-Tyr-Lys-Lys-Leu-
 Leu-Lys-Lys-Leu-Leu-Lys-Ser-Ala-Lys-Lys-Leu-
 Gly (Seq. ID #12).

33. The method of claim 32, wherein the cationic oligopeptide comprises the amino acid residue sequence:

Ala-Leu-Tyr-Lys-Lys-Leu-Leu-Lys-Lys-Leu-Leu-Lys-Se r-Ala-Lys-Lys-Leu-Gly;

wherein the amino acid residues can be d-amino acids.

34. The method of claim 4, wherein the cationic oligopeptide comprises the following sequence:

Ala-Leu-Tyr-Orn-Orn-Leu-Leu-Orn-Orn-Leu-Leu-Orn-Ser-Ala-Orn-Orn-Leu-Gly.

35. The method of claim 5, wherein the amount of the β-lactam antibiotic is a sub-inhibitory dosage.

36. The method of claim 5, wherein the β-lactam antibiotic is selected from the group consisting of a penicillin, a cephalosporin, a carbapenem, a monobactam, a cephamycin, a pyrazidon and a penem.

37. The method of claim 5, wherein the cationic oligopeptide comprises an amino acid residue sequence selected from the group consisting of:

Pro-Leu-Tyr-Lys-Lys-Ile-Ile-Lys-Lys-Leu-Leu-Glu-Ser (Seq ID #1);

Ala-Leu-Tyr-Lys-Lys-Ile-Ile-Lys-Lys-Leu-Leu-Glu-Ser-Ala-Lys-Lys-Leu-Gly (Seq. ID #5);

Ala-Leu-Tyr-Lys-Lys-Leu-Leu-Lys-Lys-Leu-Leu-Glu-Ser-Ala-Lys-Lys-Leu-Gly (Seq. ID #6);

Ala-Leu-Tyr-Lys-Lys-Leu-Leu-Lys-Lys-Leu-Leu-Lys-Ser-Ala-Lys-Lys-Leu-Gly (Seq. ID #7);

Ala-Leu-Tyr-Lys-Lys-Leu-Leu-Lys-Lys-Leu-Leu-Lys-Lys-Ala-Lys-Lys-Leu-Gly (Seq. ID #8);

Ala-Leu-Tyr-Lys-Lys-Leu-Leu-Lys-Lys-Leu-Leu-Lys-Phe-Ala-Lys-Lys-Phe-Gly (Seq. ID #10);

Lys-Trp-Lys-Leu-Tyr-Lys-Lys-Leu-Leu-Lys-Lys-Leu-Leu-Lys-Ser-Ala-Lys-Lys-Leu-Gly (Seq. ID #11); and Ala-Lys-Lys-Leu-Ala-Lys-Leu-Tyr-Lys-Lys-Leu-Lys-Lys-Leu-Leu-Lys-Ser-Ala-Lys-Lys-Leu-Gly (Seq. ID #12).

38. The method of claim 5, wherein the cationic oligopeptide comprises the amino acid residue sequence:

Ala-Leu-Tyr-Lys-Lys-Leu-Leu-Lys-Lys-Leu-Leu-Lys-Ser-Ala-Lys-Lys-Leu-Gly, wherein the amino acid residues can be d-amino acids.

39. The method of claim 5, wherein the cationic oligopeptide comprises the amino acid residue sequence:

Ala-Leu-Tyr-Orn-Orn-Leu-Leu-Orn-Orn-Leu-Leu-Orn-Ser-Ala-Orn-Orn-Leu-Gly.

40. A method for treating a bacterial infection caused by *Escherichia coli* comprising administering to a patient a therapeutically effective amount of a composition comprising: (a) cefepime and (b) a C-13 peptide of human platelet factor-4 comprising the amino acid residue sequence:

Pro-Leu-Tyr-Lys-Lys-Ile-Ile-Lys-Lys-Leu-Leu-Glu-Ser; (Seq. I.D. #1)

for a time period sufficient to inhibit the growth of the bacteria.

41. A method for treating a bacterial infection caused by *Escherichia coli* comprising administering to a patient a therapeutically effective amount of a composition comprising: (a) cefepime and (b) a cationic oligopeptide comprising the amino acid residue sequence:

Ala-Leu-Tyr-Lys-Lys-Leu-Leu-Lys-Lys-Leu-Leu-Lys-Ser-Ala-Lys-Lys-Leu-Gly (Seq. I.D. #7);

for a time period sufficient to inhibit the growth of the bacteria.

42. A method for treating a bacterial infection caused by *Escherichia coli* comprising administering to a patient a therapeutically effective amount of a composition comprising: (a) cefepime and (b) a cationic oligopeptide comprising the amino acid residue sequence:

Ala-Leu-Tyr-Lys-Lys-Leu-Leu-Lys-Lys-Leu-Leu-Lys-Ser-Ala-Lys-Lys-Leu-Gly;

wherein all the amino acid residues are d-amino acids, for a time period sufficient to inhibit the growth of the bacteria.

43. A method for treating a bacterial infection caused by *Escherichia coli* comprising administering to a patient a therapeutically effective amount of a composition comprising: (a) cefepime and (b) a cationic oligopeptide comprising the amino acid residue sequence:

Ala-Leu-Tyr-Lys-Lys-Leu-Leu-Lys-Lys-Leu-Leu-Glu-Ser-Ala-Lys-Lys-Leu-Gly (Sequence I.D. #6);

for a time period sufficient to inhibit the growth of the bacteria.

44. A method for treating a bacterial infection caused by *Escherichia coli* comprising administering to a patient a therapeutically effective amount of a composition comprising: (a) cefepime and (b) a cationic oligopeptide comprising the amino acid residue sequence:

Ala-Leu-Tyr-Orn-Orn-Leu-Leu-Orn-Orn-Leu-Leu-Orn-Ser-Ala-Orn-Orn-Leu-Gly for a time period sufficient to inhibit the growth of the bacteria.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:1:

Pro Leu Tyr Lys Lys Ile Ile Lys Lys Leu Leu Glu Ser
     1               5                        10

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:2:

Pro Leu Tyr Lys Pro Lys Ile Ile Lys Pro Lys Leu Leu Glu Ser
     1               5                        10                    15

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide (iii) HYPOTHETICAL: YES (xi) SEQUENCE DESCRIPTION: SEQ ID NO:3:

Pro Leu Lys Lys Tyr Ile Ile Lys Lys Glu Leu Leu Ser
1               5                   10

(2) INFORMATION FOR SEQ ID NO:4:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (iii) HYPOTHETICAL: YES (xi) SEQUENCE DESCRIPTION: SEQ ID NO:4:

Pro Leu Tyr Lys Lys Pro Ile Lys Lys Pro Leu Glu Ser
1               5                   10

(2) INFORMATION FOR SEQ ID NO:5:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (iii) HYPOTHETICAL: YES (xi) SEQUENCE DESCRIPTION: SEQ ID NO:5:

Ala Leu Tyr Lys Lys Ile Ile Lys Lys Leu Leu Glu Ser Ala Lys Lys
1               5                   10                  15

Leu Gly (2) INFORMATION FOR SEQ ID NO:6:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (iii) HYPOTHETICAL: YES (xi) SEQUENCE DESCRIPTION: SEQ ID NO:6:

Ala Leu Tyr Lys Lys Leu Leu Lys Lys Leu Leu Glu Ser Ala Lys Lys
1               5                   10                  15

Leu Gly (2) INFORMATION FOR SEQ ID NO:7:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (iii) HYPOTHETICAL: YES (xi) SEQUENCE DESCRIPTION: SEQ ID NO:7:

Ala Leu Tyr Lys Lys Leu Leu Lys Lys Leu Leu Lys Ser Ala Lys Lys
1               5                   10                  15

Leu Gly ( 2 ) INFORMATION FOR SEQ ID NO:8:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:8:

```
Ala  Leu  Tyr  Lys  Lys  Leu  Leu  Lys  Lys  Leu  Leu  Lys  Lys  Ala  Lys  Lys
 1                  5                            10                           15
Leu  Gly
```

( 2 ) INFORMATION FOR SEQ ID NO:9:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:9:

```
Ala  Leu  Tyr  Arg  Arg  Leu  Leu  Arg  Arg  Leu  Leu  Arg  Ser  Ala  Arg  Arg
 1                  5                            10                           15
Leu  Gly
```

( 2 ) INFORMATION FOR SEQ ID NO:10:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:10:

```
Ala  Leu  Tyr  Lys  Lys  Leu  Leu  Lys  Lys  Leu  Leu  Lys  Phe  Ala  Lys  Lys
 1                  5                            10                           15
Phe  Gly
```

( 2 ) INFORMATION FOR SEQ ID NO:11:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:11:

```
Lys  Trp  Lys  Leu  Tyr  Lys  Lys  Leu  Leu  Lys  Lys  Leu  Leu  Lys  Ser  Ala
 1                  5                            10                           15
Lys  Lys  Leu  Gly
                 20
```

( 2 ) INFORMATION FOR SEQ ID NO:12:

( i ) SEQUENCE CHARACTERISTICS:
        ( A ) LENGTH: 23 amino acids

-continued (B) TYPE: amino acid
(D) TOPOLOGY: linear (ii) MOLECULE TYPE: peptide (iii) HYPOTHETICAL: YES (xi) SEQUENCE DESCRIPTION: SEQ ID NO:12:

Ala Lys Lys Leu Ala Lys Leu Tyr Lys Lys Leu Leu Lys Lys Leu Leu
1               5                   10                  15

Lys Ser Ala Lys Lys Leu Gly
            20